United States Patent
Zhou et al.

(10) Patent No.: US 9,522,915 B2
(45) Date of Patent: Dec. 20, 2016

(54) METHOD FOR PREPARING AN IMPORTANT INTERMEDIATE OF LINAGLIPTIN

(71) Applicant: 2Y-CHEM, LTD., Shanghai (CN)

(72) Inventors: Yanfeng Zhou, Shanghai (CN); Yong Liu, Shanghai (CN); Xuezhang Wang, Shanghai (CN); Xungui He, Shanghai (CN); Yuan Wang, Shanghai (CN)

(73) Assignee: 2Y-CHEM, LTD., Shanghai (CN)

( * ) Notice: Subject to any disclaimer, the term of this patent is extended or adjusted under 35 U.S.C. 154(b) by 0 days.

(21) Appl. No.: 14/436,566

(22) PCT Filed: Oct. 17, 2013

(86) PCT No.: PCT/CN2013/085390
§ 371 (c)(1),
(2) Date: Apr. 17, 2015

(87) PCT Pub. No.: WO2014/059938
PCT Pub. Date: Apr. 24, 2014

(65) Prior Publication Data
US 2015/0274728 A1    Oct. 1, 2015

(30) Foreign Application Priority Data

Oct. 19, 2012  (CN) .......................... 2012 1 0403422

(51) Int. Cl.
*C07D 473/04* (2006.01)
*C07D 473/06* (2006.01)

(52) U.S. Cl.
CPC ........... *C07D 473/04* (2013.01); *C07D 473/06* (2013.01)

(58) Field of Classification Search
CPC .......................... C07D 473/04; C07D 473/10
See application file for complete search history.

(56) References Cited

FOREIGN PATENT DOCUMENTS

| DE | CA 2496249 A1 * | 3/2004 | ........... A61K 9/0095 |
| JP | 2007262040 A | 10/2007 | |
| WO | 2004018468 A2 | 3/2004 | |
| WO | 2006048427 A1 | 3/2006 | |

OTHER PUBLICATIONS

Ooi, Takashi. Angew Chem Int. Ed. 2007. 46, 4222-4266.*
Eckhardt, Matthias. Supporting Information. J. Med. Chem. 2007. 50. S1-S18.*
Eckhardt, M. et al., "8-(3-(R)-Aminopiperidin-1-yl)-7-but-2-ynyl-3-methyl-1-(4-methyl-quinazolin-2-ylmethyl)-3,7-dihydropurine-2,6-dione (Bl 1356), a Highly Potent, Selective, Long-Acting, and Orally Bioavailable DPP-4 Inhibitor for the Treatment of Type 2 Diabetes," Journal of Medicinal Chemistry, 2007, vol. 50(26), pp. 6450-6453.

* cited by examiner

*Primary Examiner* — Golam M M Shameem
*Assistant Examiner* — Laura Daniel
(74) *Attorney, Agent, or Firm* — Ping Wang; Andrews Kurth Kenyon LLP

(57) ABSTRACT

The present invention discloses an improved process for preparing an important intermediate of linagliptin. In particular, disclosed are a process for preparing a compound V which is an important intermediate of linagliptin and has the structure V, and an industrial process of preparing linagliptin having excellent chemical and optical purities, which is an inhibitor of dipeptidyl peptidase-4 (DPP-IV), from the compound V. The process employs a phase-transfer catalyst, is high in yield, easy and simple to handle, environmentally friendly, suitable for industrial mass production, and can be implemented by a "one-pot process".

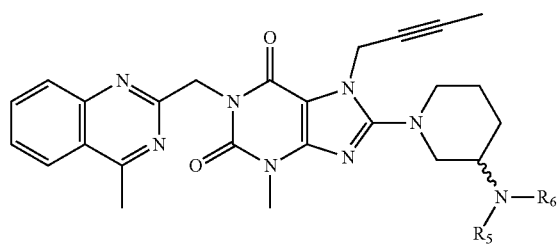

15 Claims, No Drawings

METHOD FOR PREPARING AN IMPORTANT INTERMEDIATE OF LINAGLIPTIN

This application is a national stage application of International Patent Application No. PCT/CN2013/085390, filed Oct. 17, 2013, which claims priority to Chinese Patent Application No. 201210403422.4, filed Oct. 19, 2012. The entirety of the aforementioned applications is incorporated herein by reference.

FIELD OF THE INVENTION

The present invention relates to a process for preparing a dipeptidyl peptidase-4 (DPP-IV) inhibitor, and more particularly, to an improved process for preparing an important intermediate of linagliptin.

BACKGROUND OF THE INVENTION

Linagliptin has a IUPAC name of 8-[(3R)-3-aminopiperidin-1-yl]-7-(but-2-yn-1-yl)-3,7-dihydro-3-methyl-1-[(4-methylquinazolin-2-yl)methyl]-1H-purine-2,6-dione, and a molecular structure formula as follows:

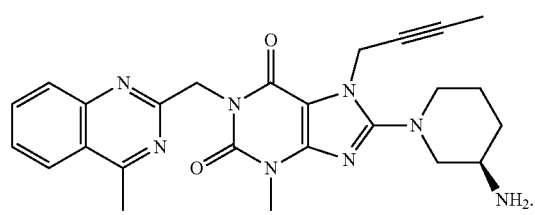

I

Linagliptin is an oral hypoglycemic drug developed by Boehringer Ingelheim Pharmaceuticals Inc., Germany, which is approved by the US FDA on May 2, 2011 and marketed under the trade name Tradjenta. Linagliptin is used to control the glycemic level of patients primarily by inhibiting DPP-IV, and further used to control the glycemic level of type 2 diabetic patients in conjunction with diet and exercise.

WO 2004/018468 discloses synthetic examples of 8-[3-aminopiperidin-1-yl]xanthines, the tautomers, non-enantiomers, racemates and salts thereof.

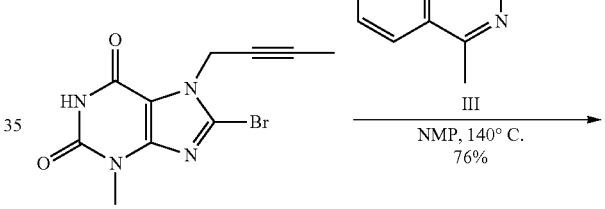

VII

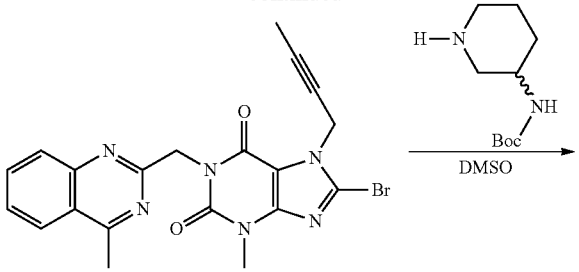

VIII

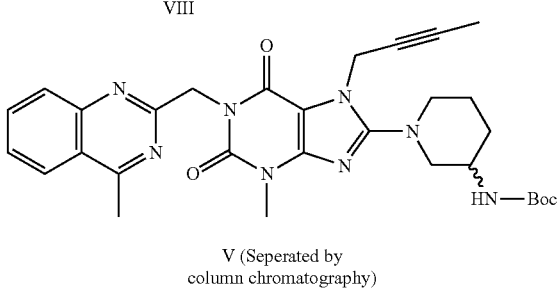

V (Seperated by column chromatography)

WO 2006/048427 discloses an improved process for preparing chiral 8-[3-aminopiperidin-1-yl]xanthines, their enantiomers and their physiologically tolerable salts.

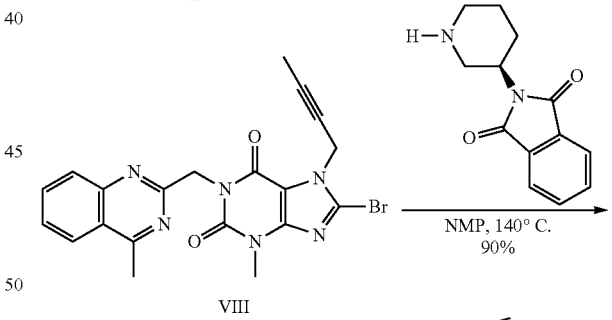

VII

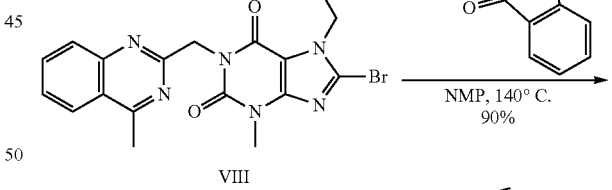

VIII

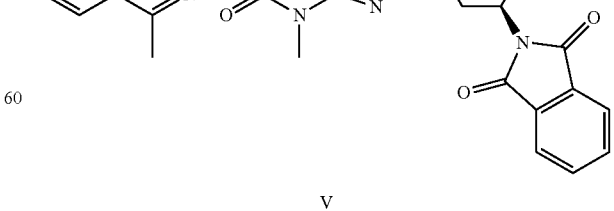

V

In both of the above two processes, 8-[3-aminopiperidin-1-yl]xanthines are prepared by reacting the xanthine precursor VII successively with 2-chloromethyl-4-methylquinazoline (III) and 3-aminopiperidine derivative via N-alkylation reaction to give the corresponding N-protected Linagliptin derivative (V), which is finally deprotected to prepare Linagliptin (I).

In the above preparation processes, the solvent used is N,N-dimethylformamide (DMF), dimethylsulfoxide (DMSO), N-methylpyrrolidone (NMP), or the like, which are water-soluble, the intermediate in each step requires separation and purification, in which water is added directly for crystallization, and the solvent is hardly to be recycled, causing a great pollution by liquid waste. In addition, the separation of the intermediates is complicated and has along production cycle and a high energy consumption, which is difficult to satisfy the requirement of "green chemistry" in industrial production. Furthermore, the final product obtained by the above synthetic process needs to be isolated and purified by column chromatography, which is difficult to meet the demand for industrial mass production.

Therefore, there is still a need for a process for preparing linagliptin derivatives with high yield, simple operation, which is environmentally friendly and suitable for industrial mass production, so that it is possible to prepare the linagliptin with excellent chemical and optical purity in industrial mass production.

SUMMARY OF THE INVENTION

An object of the present invention to provide a process for preparing linagliptin derivative of the following formula V, wherein, in the presence of a phase transfer catalyst (PTC) and a cocatalyst at a temperature of 0 to 160° C., preferably 40 to 120° C. in a solvent, Compound VI as a starting material reacts with Compound II via 7-N-substitution reaction, with Compound III via 1-N-substitution reaction, and then with Compound IV via 8-C-substitution reaction, to give Compound V, wherein, $X_1$, $X_2$ and $X_3$ are each a leaving group, and each independently selected from the group consisting of a halogen, such as fluorine, chlorine or bromine, and a sulfonate group, such as methylsulfonyloxy (MsO), phenylsulfonyloxy, p-toluenesulfonyloxy, p-chlorophenylsulfonyloxy, benzylsulfonate, 2-(4-nitrophenylethyl)sulfonate or trifluoromethylsulfonyloxy, $X_1$ is preferably bromine, $X_2$ is preferably chlorine, $X_3$ is preferably bromine or chlorine, $R_5$ and $R_6$ are each a N-protecting group, and are each independently H, C1-C16 alkoxycarbonyl, C6-C18 aryl C1-C16 alkoxycarbonyl, benzyl, p-methoxybenzyl, p-methylbenzyl, p-chlorobenzyl, p-bromobenzyl, p-nitrobenzyl, diphenylmethyl, 2,4-dimethoxybenzyl, 2-hydroxybenzyl, bis(4-methoxyphenyl)methyl, triphenylmethyl, (4-methoxyphenyl)diphenylmethyl, 9-phenylfluorenyl, formyl, acetyl, chloroacetyl, dichloroacetyl, trichloroacetyl, phenylacetyl, phenylpropionyl, benzoyl, p-phenylbenzoyl, phthaloyl, 4-nitrophthaloyl, dithiosuccinyl, tetrachlorophthaloyl, p-toluenesulfonyl, benzenesulfonyl, methanesulfonyl, 2,4,6-trimethoxybenzenesulfonyl, pentamethylbenzenesulfonyl, 4-methoxybenzenesulfonyl, 2,4,6-trimethylbenzenesulfonyl, 2,6-dimethoxy-4-methyl-benzenesulfonyl, 2-nitrobenzenesulfonyl, 4-nitrobenzenesulfonyl, 2,4-dinitrobenzenesulfonyl, pyridine-2-sulfonyl, 2-(trisilyl) ethylsulfonyl, 9-anthracenesulfonyl, benzylsulfonyl, trifluoromethylsulfonyl, benzoylsulfonyl, or tert-butylsulfonyl and the like. The C1-C16 alkoxycarbonyl may be methoxycarbonyl, ethoxycarbonyl, propoxycarbonyl, isopropoxycarbonyl, butoxycarbonyl, iso-butoxycarbonyl or tert-butoxycarbonyl, and the C6-C18 aryl C1-C16 alkoxycarbonyl may be benzyloxycarbonyl or 9-fluorenyl-methoxycarbonyl (Fmoc). Preferably, $R_5$ and $R_6$ are each independently H, t-butyloxycarbonyl, 9-fluorenylmethoxycarbonyl or phthaloyl.

The 3-amino in Compound IV is a chiral center, and Compound IV may be R-isomer, S-isomer or racemate. Compound IV may be a free base or a piperidine salt formed with an organic or inorganic acid. The piperidine salt is one or more selected from the group consisting of hydrochloride, hydrobromide, phosphate, nitrate, sulfate, acetate, 2,2-dichloroacetate, adipate, ascorbate (D- or L-form thereof), aspartate, benzenesulfonate, benzoate, 4-acetamido-benzoate, camphorate, camphor-10-sulfonate, decanoic acid salt (caprate), hexanoic acid salt (caproate), octanoic acid salt (caprylate), carbonate, cinnamate, citrate, cyclamate, dodecylsulfate, ethane-1,2-disulfonate, ethanesulfonate, 2-hydroxy-ethanesulfonate, formate, fumarate, mucic acid salt, gentisic acid salt, glucoheptonic acid salt, gluconate, glucuronate, glutamate, glutarate, 2-oxo-glutarate, glycerophosphate, glycolate, hippurate, isobutyrate, lactate, lactobionic acid salt, laurate, maleate, malate, malonate, mandelate, methanesulfonate, naphthalene-1,5-disulfonate, naphthalene-2-sulfonate, 1-hydroxy-2-naphthoate, nicotinate, oleate, orotic acid salt, oxalate, palmitate, dihydroxy naphthoic acid salt, propionate, pyroglutamate, salicylate, 4-aminosalicylate, sebacate, stearate, succinate, tartrate, thiocyanate, tosylate and undecylenic acid salt.

The phase transfer catalyst (PTC) may be a compound having the following structure:
(1) the phase transfer catalyst (PTC) may have the structure of $R_1R_2R_3R_4N^+X_4^-$,
wherein,
$R_1$, $R_2$, $R_3$ and $R_4$ are each independently C1-C18 alkyl or C6-C18 aryl,
$X_4$ is halogen, such as fluorine, chlorine or bromine, or bisulfate or hydroxy,
the specific examples thereof are one or more selected from the group consisting of cetyltrimethylammonium bromide, dicetyldimethylammonium bromide, dicetyldimethylammonium chloride, dioctadecyldimethylammonium bromide, dioctadecyldimethylammonium chloride, benzyltriethylammonium chloride, tributylmethylammonium chloride, tributylmethylammonium bromide, triethylammoniumbromide, triethylammoniumchloride, tripropylmethylammonium chloride, trioctylmethylammonium chloride, myristyltrimethylammonium chloride, tripropylmethylammonium bromide, tetrapropylammonium chloride, tetrapropylammonium bromide, tetraethylammonium bromide, tetraethylammonium chloride, tetrabutylammonium bisulfate, didecyldimethylammonium chloride, didecyldimethylammonium bromide, tetrabutylammonium bromide, benzyltributylammonium chloride and benzyltributylammonium bromide, or one or more selected from the group consisting of tetramethylammonium hydroxide, trimethylethylammonium hydroxide, tetrabutylammonium hydroxide and trimethylbenzylammonium hydroxide;
(2) the phase transfer catalyst (PTC) may be a polyether, such as a linear polyethylene glycol of $H(OCH_2CH_2)_nOH$, a linear polyethylene glycol dialkyl ether of $R'_1(OCH_2CH_2)_nOR'_2$ and the like,
wherein,
$R'_1$ and $R'_2$ are each independently C1-C18 alkyl or C6-C18 aryl,
n is an integer of 1-44;
(3) the phase transfer catalyst (PTC) may be a tertiary amine of $R''_1R''_2R''_3N$,
wherein,
$R''_1$, $R''_2$ and $R''_3$ are each independently C1-C18 alkyl or C6-C18 aryl group; the specific examples of the tertiary amine PTC are pyridine, triethylamine and the like;
(4) the phase transfer catalyst (PTC) may be a quaternary phosphine salt of $R'''_1R'''_2R'''_3R'''_4P^+X'^-_4$,
wherein,
$R'''_1$, $R'''_2$, $R'''_3$ and $R'''_4$ are each independently C1-C18 alkyl or C6-C18 aryl group, and $X'^-_4$ is halogen, such as fluorine, chlorine or bromine, or bisulfate,
specific examples thereof may be one or more selected from the group consisting of triphenylmethylphosphine bromide, triphenylmethylphosphine chloride, triphenylethylphosphine chloride, triphenylethylphosphine bromide, triphenylpropylphosphine chloride, triphenylpropylphosphine bromide, triphenylbenzylphosphine chloride, triphenylbenzylphosphine bromide, triphenyldodecylphosphine chloride, triphenyldodecylphosphine bromide, triphenylcetylphosphine chloride, triphenylcetylphosphine bromide, tetrabutylphosphine bromide, tetrabutylphosphine chloride, tetraphenylphosphine bromide, cetyltributylphosphine bromide and the like.

The phase transfer catalyst (PTC) is used in an amount of 0.05 to 1.0 molar equivalents, preferably 0.2 to 0.5 molar equivalents based on the amount of the starting material of Compound VI.

The cocatalyst has a structure of $\overset{M}{\oplus}\overset{X_5}{\ominus}$, and is used in an amount of 0.01 to 1.0 molar equivalents based on the amount of the starting material of Compound VI, wherein, $X_5$ is an ion with negative charge, preferably halogen ion, more preferably iodine or bromine ion; M is an ionic group with positive charge or a metal ion, preferably $NH_4^+$ or an alkali metal ion, more preferably potassium or sodium ion. The specific examples thereof are lithium bromide, sodium bromide, potassium bromide, lithium iodide, sodium iodide, ammonium chloride, sodium bromide, ammonium iodide or potassium iodide. More preferably, it is potassium iodide or sodium iodide.

The solvent may be, for example, one or more selected from the group consisting of tetrahydrofuran (THF), 2-methyltetrahydrofuran, methyl isobutyl ketone (MIBK), n-butanol, t-butanol, isoamyl alcohol, toluene, xylene, chlorobenzene, ethyl acetate, isopropyl acetate, propyl acetate, butyl acetate, isobutyl acetate, methyl tert-butyl ether, isopropyl ether, diphenyl ether, cyclohexane, n-hexane, n-heptane, mixed-heptane, iso-octane, acetonitrile, dichloromethane, chloroform, 1,2-dichloroethane and the like, preferably one or more selected from the group consisting of 2-methyltetrahydrofuran, tetrahydrofuran, toluene, ethyl acetate, isopropyl acetate, propyl acetate, butyl acetate and isobutyl acetate.

Then the protecting group on 3-amino is removed from the obtained compound of formula V, to get linagliptin. The process for removing the protecting group of amino may be a conventional technique known in the art, e.g., the processes described in WO 2004/018468 and WO 2006/048427.

Specifically, the process for preparing the linagliptin derivative of formula V may be conducted according to the following Scheme 1 or Scheme 2:

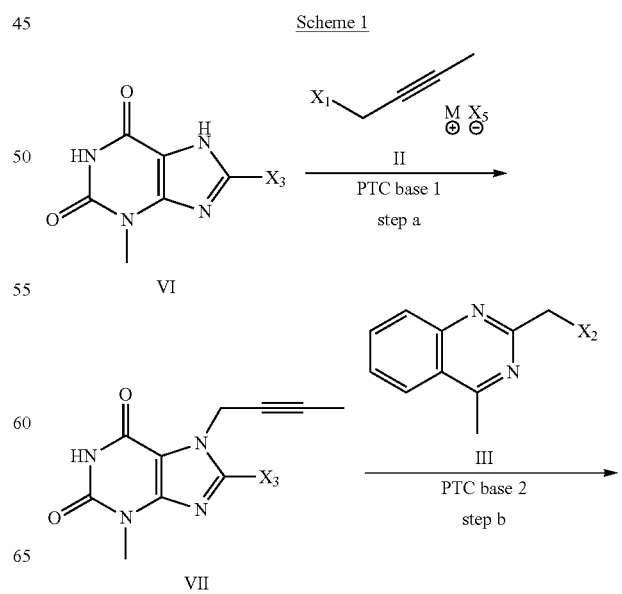

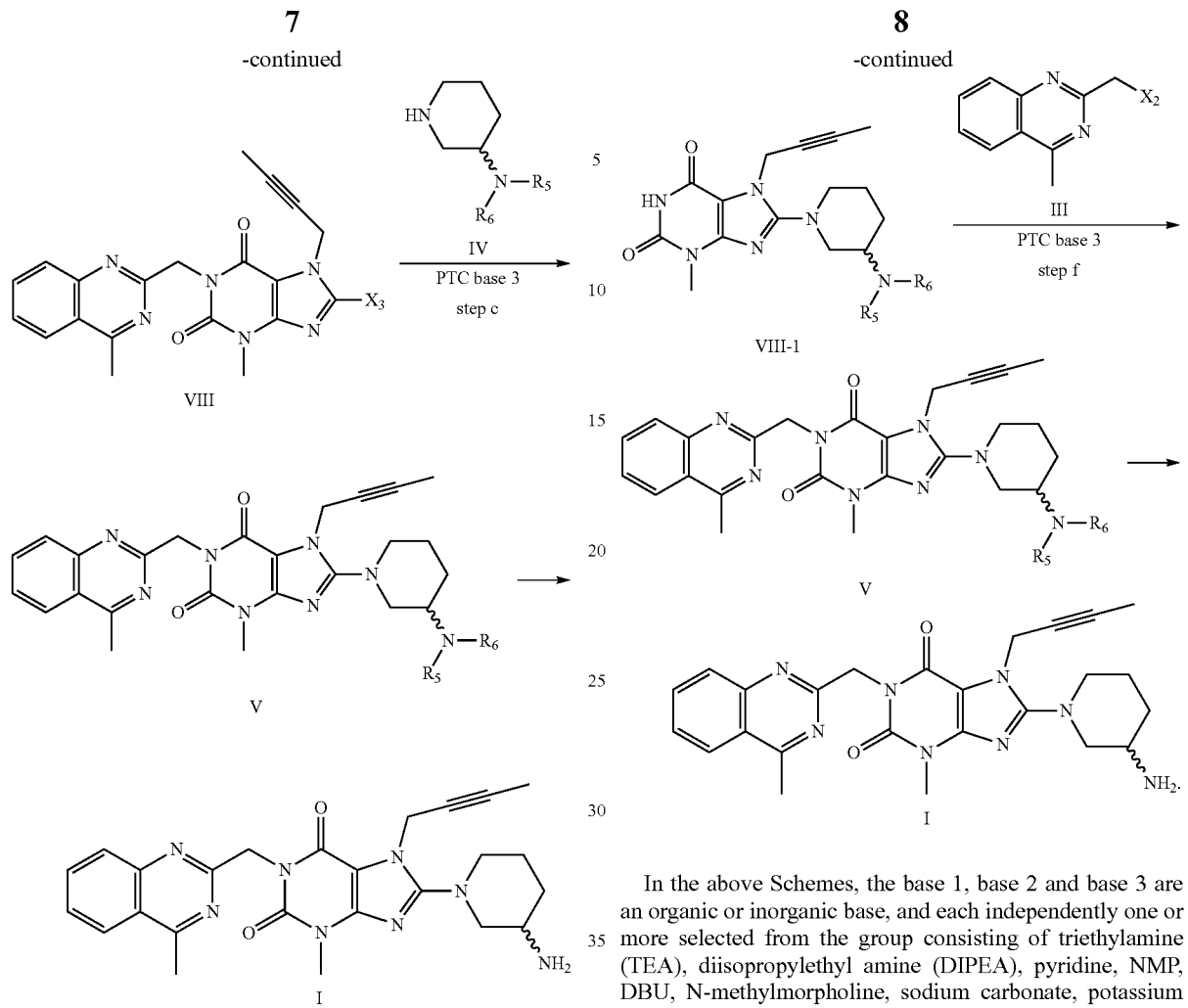

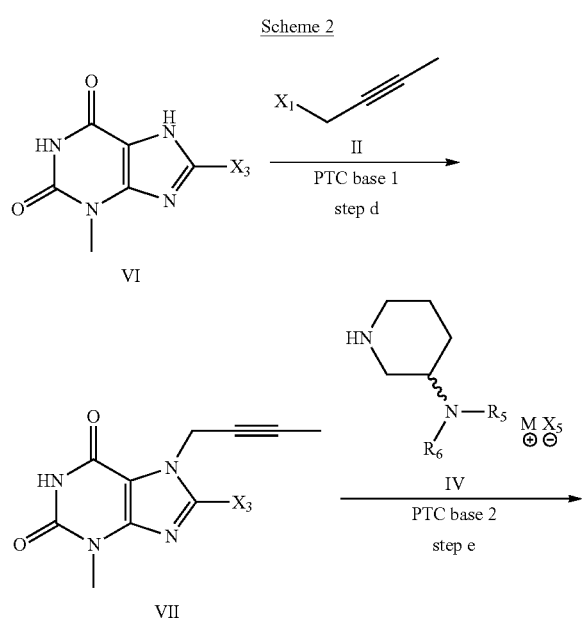

In the above Schemes, the base 1, base 2 and base 3 are an organic or inorganic base, and each independently one or more selected from the group consisting of triethylamine (TEA), diisopropylethyl amine (DIPEA), pyridine, NMP, DBU, N-methylmorpholine, sodium carbonate, potassium carbonate, sodium bicarbonate, potassium bicarbonate, cesium carbonate, disodium hydrogen phosphate, sodium hydroxide, potassium hydroxide and sodium hydride.

In the Scheme 1 or 2, the solvents used in the steps a to f are the same as above, and the same or different solvents may be used in each step. When a same solvent is used in various steps, the process of the present invention may be implemented by "one-pot process".

Compounds III and IV are prepared according to the processes disclosed in WO 2006/048427 and JP 2007/262040. Compound VI is prepared according to the process described in *Journal of Medicinal Chemistry*, 2009, vol. 52, No. 20, 6433-6445. Compound II is commercially available, or may be prepared from 2-butyn-1-ol as a starting material, according to the processes described in *Journal of American Chemical Society*, 2009, vol. 131, No. 25, 8772-8774, and *Tetrahedron Letters*, 2003, vol. 44, No. 46, 8417-8420 and the like.

Among others, the molar ratio of the reactants in steps a and d is VI:II:base 1=1:(0.8 to 1.5):(1.0 to 5.0); and the reaction time is 0.5 to 48 hours;

the molar ratio of the reactants in step b is VII:III:base 2=1.0:(0.8 to 1.5):(1.0 to 5.0); and the reaction time is 0.5 to 48 hours;

the molar ratio of the reactants in step c is VIII:IV:base 3=1.0:(0.8 to 1.5):(1.0 to 5.0); and the reaction time is 0.5 to 72 hours;

the molar ratio of the reactants in step e is VII:IV:base 2=1.0:(0.8 to 1.5):(1.0 to 5.0); and the reaction time is 0.5 to 72 hours;

the molar ratio of the reactants in step f is VIII-1:III:base 3=1.0:(0.8 to 1.5):(1.0 to 5.0); and the reaction time is 0.5 to 72 hours.

Technical Effect

The preparation process of the present invention provides the following advantages compared to the conventional process.

The use of the phase transfer catalyst (PTC) allows the respective reaction step that forms C—N bond in the Schemes 1 and 2 to be conducted smoothly in a non-aqueous solvent, such as tetrahydrofuran (THF), 2-methyltetrahydrofuran, methyl isobutyl ketone (MIBK), n-butanol, t-butanol, isoamyl alcohol, toluene, xylene, chlorobenzene, ethyl acetate, isopropyl acetate, propyl acetate, butyl acetate, isobutyl acetate, methyl tert-butyl ether, isopropyl ether, cyclohexane, n-hexane, n-heptane, mixed-heptane, isooctane, acetonitrile, dichloromethane, chloroform, 1,2-dichloroethane and the like. In these solvents, the introduction of PTC allows the Compounds VII, VIII, VIII-1 and V in the Schemes 1 and 2 to be obtained with a relatively high purity (95% or more) and yield (85% or more), while the absence of PTC would cause the Compounds VIII, VIII-1 and V in the Schemes 1 and 2 to be hardly prepared.

The introduction of PTC may avoid the use of water-soluble solvents, e.g. NMP, DMF, DMSO, DMAC, etc., which are necessary for the conventional processes and difficult to be recycled. The preparation process of the present invention provides the possibility of recovering the solvent, and thus reduces the cost. Meanwhile, the preparation process of the present invention reduces the waste emission, and thus realizes the concept of green chemistry and environmental friendship, and it is more suitable for industrial production.

The use of PTC may reduce the O-alkylated impurities, which are inevitably generated (~around 5%) in the conventional processes and hardly to be removed, to be 1% or less, and thus effectively reduce the difficulty in purification of the product.

The skillfully use of PTC allows a plural of reaction steps for forming C—N bond in the Schemes 1 and 2 to be conducted in a single solvent to realize the one-pot synthesis of xanthine precursor (Compound V).

The "one-pot process" catalyzed with PTC for preparing xanthine precursor (Compound V) is simple and does not need isolation of intermediates with a shortened production cycle and a reduced equipment requirements, and thus it is more suitable for industrial production.

The xanthine precursor (Compound V) obtained by the "one-pot process" catalyzed with PTC can be deprotected of the piperidin-3-amino protecting group without the separation and purification by column chromatography to prepare Linagliptin. The overall yield of the "one-pot process" for preparing xanthine precursor (Compound V) is up to 75%. The purity of the obtained Compound V is up to 96%.

DESCRIPTION OF THE PREFERRED EMBODIMENTS

Without further detailed description, those skilled in the art can maximize the use of the present invention in virtue of the foregoing description. Thus, the following examples are provided merely to further illustrate the present invention, and they do not meant in any way to limit the scope of the present invention. Among others, Examples 1-9 are synthetic processes conducted stepwisely, and Examples 10-23 are synthetic processes using "one-pot process", and Example 24 is an example for obtaining linagliptin from Compound V (an important intermediate of linagliptin) through deprotection of amino.

EXAMPLE 1

Synthesis of 2-chloromethyl-4-methylquinazoline (Compound III)

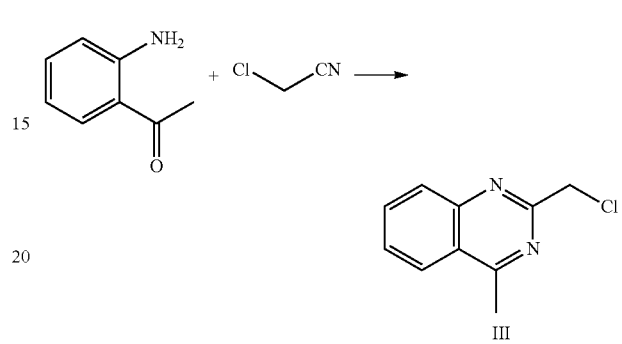

For the specific preparation process, please refer to the PCT Application with the Publication No. WO 2006/048427.

EXAMPLE 2

Synthesis of (R)-3-tert-butoxycarbonylaminopiperidine (Compound IV)

The compound was prepared according to the process disclosed in JP 2007/262040 for synthesizing (R)-3-tert-butoxycarbonylaminopiperidine from the starting material of D-glutamic acid.

EXAMPLE 3

Synthesis of (R)-3-phthalimidopiperidine (Compound IV)

The compound was prepared according to the process disclosed in WO 2006/048427 for synthesizing (R)-3-phthalimidopiperidine (Compound IV) from the starting material of 3-aminopyridine.

EXAMPLE 4

Synthesis of 3-methyl-7-(2-butyn-1-yl)-8-bromoxanthine (Compound VII)

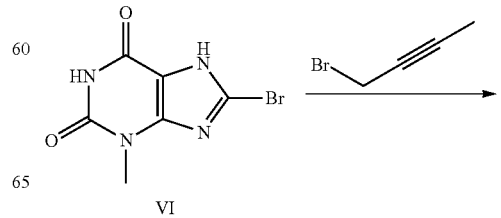

-continued

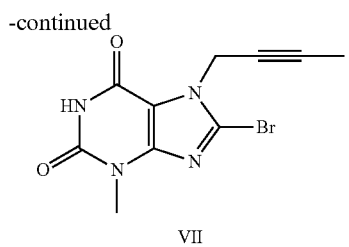

VII 1 g (0.0041 mol) of 8-bromo-3-methyl-1H-purine-2,6 (3H,7H)-dione (Compound VI, prepared according to the process disclosed in *Journal of Medicinal Chemistry*, 2009, vol 52, No. 20, 6433-6445), tetrahydrofuran (50 mL), diisopropylethylamine (DIPEA, base 1, 0.68 g, 0.0053 mol), 1-bromo-2-butyne (Compound II, 0.54 g, 0.0041 mol) and potassium iodide (cocatalyst $MX_5$, 0.014 g, 0.084 mmol) were added to a reaction flask under nitrogen protection. The tributylmethylammonium chloride (PTC, 0.47 g, 0.002 mol) was added to the above mixture. The mixture in the reaction flask was heated to reflux for 1 to 2 hours, cooled to room temperature, and added with 100 mL of water. After filtration, the filter cake was collected, and dried at 45° C. to give 3-methyl-7-(2-butyn-1-yl)-8-bromoxanthine (Compound VII).

Yield: 1.13 g (93% of theoretical value)

MS: $[M+H]^+$=297/299

$^1$H-NMR (400 MHz, DMSO): δ 1.80 (s, 3H), 3.31 (s, 3H), 5.06 (s, 2H), 11.31 (s, 1H).

The Compound VII can also be prepared by the following processes.

The same process as that in Example 4 was performed, except that tetrahydrofuran (50 mL) was replaced by 2-methyltetrahydrofuran (50 mL), and potassium iodide (cocatalyst $MX_5$, 0.014 g, 0.084 mmol) was not added. The mixture in the reaction flask was heated to reflux for ~4 hours.

Yield: 1.09 g (90% of theoretical value)

The same process as that in Example 4 was performed, except that tetrahydrofuran (50 mL) was replaced by ethyl acetate (50 mL), tributylmethylammonium chloride (PTC, 0.47 g, 0.002 mol) was replaced by triethylamine (PTC, 0.08 g, 0.00082 mol), di-isopropylethylamine (DIPEA, base 1, 0.68 g, 0.0053 mol) was replaced by triethylamine (base 1, 0.53 g, 0.0053 mol), and potassium iodide (cocatalyst $MX_5$, 0.014 g, 0.084 mmol) was not added.

Yield: 0.63 g (52% of theoretical value)

The same process as that in Example 4 was performed, except that tetrahydrofuran (50 mL) was replaced by toluene (50 mL), tributylmethylammonium chloride (PTC, 0.47 g, 0.002 mol) was replaced by polyethylene glycol dimethyl ether (PTC, $CH_3O(CH_2CH_2O)_nCH_3$, n=3-8, 0.5 g, 0.002 mol), and potassium iodide (cocatalyst $MX_5$, 0.014 g, 0.084 mmol) was not added. The mixture in the reaction flask was heated to reflux for ~6 hours.

Yield: 0.49 g (41% of theoretical value)

The same process as that in Example 4 was performed, except that tetrahydrofuran (50 mL) was replaced by isopropyl acetate (80 mL), di-isopropylethylamine (DIPEA, base 1, 0.68 g, 0.0053 mol) was replaced by sodium bicarbonate (base 1, 1.89 g, 0.022 mol), tributylmethylammonium chloride (PTC, 0.47 g, 0.002 mol) was replaced by tetrabutylphosphine bromide (PTC, 1.39 g, 0.0041 mol), and potassium iodide (cocatalyst $MX_5$, 0.014 g, 0.084 mmol) was not added. The mixture in the reaction flask was heated to reflux for ~12 hours, and cooled to room temperature, followed by addition of 150 mL of water.

Yield: 0.68 g (56% of theoretical value)

EXAMPLE 5

Synthesis of 1-[(4-methyl-quinazolin-2-yl)methyl]-3-methyl-7-(2-butyn-1-yl)-8-bromoxanthine (Compound VIII)

3-methyl-7-(2-butyn-1-yl)-8-bromoxanthine (Compound VII, 1.34 g, 0.0045 mol), potassium carbonate (base 2, 1.42 g, 0.0103 mol), 2-chloromethyl-4-methylquinazoline (Compound III, 0.87 g, 0.0045 mol), tributylmethylammonium chloride (PTC, 0.53 g, 0.002 mol) and 2-methyltetrahydrofuran (50 mL) were added to a reaction flask. The mixture was heated to reflux for 3 to 5 hours, cooled to room temperature, and added with 100 mL of water. After filtration, the filter cake was collected, and dried at 45° C. to give 1-[(4-methyl-quinazolin-2-yl)methyl]-3-methyl-7-(2-butyn-1-yl)-8-bromo xanthine (Compound VIII).

Yield: 1.78 g (87.1% of theoretical value)

MS: $[M+H]^+$=453/455

$^1$H-NMR (400 MHz, DMSO): δ 1.79 (t, J=2.3 Hz, 3H), 2.89 (s, 3H), 3.44 (s, 3H), 5.11 (q, J=2.2 Hz, 2H), 5.35 (s, 2H), 7.67 (m, 1H), 7.80 (d, J=8.3 Hz, 1H), 7.75 (m, 1H), 8.24 (d, J=8.1 Hz, 1H).

The Compound VIII can also be prepared by the following processes.

The same process as that in Example 5 was performed, except that 2-methyltetrahydrofuran (50 mL) was replaced by tetrahydrofuran (50 mL), and sodium iodide (cocatalyst $MX_5$, 0.01 g, 0.09 mmol) was additionally added.

Yield: 1.76 g (86.6% of theoretical value)

The same process as that in Example 5 was performed, except that tributylmethylammonium chloride (PTC, 0.53 g, 0.002 mol) was replaced by triethylamine (PTC, 0.09 g, 0.0009 mol), and 2-methyltetrahydrofuran (50 mL) was replaced by 2-methyltetrahydrofuran (80 mL). The mixture was heated to reflux for ~32 hours, and cooled to room temperature, followed by addition of 160 mL of water.

Yield: 1.25 g (61.4% of theoretical value)

The same process as that in Example 5 was performed, except that tributylmethylammonium chloride (PTC, 0.53 g, 0.002 mol) was replaced by polyethylene glycol dimethyl ether (PTC, $CH_3O(CH_2CH_2O)_nCH_3$, n=3-8, 0.5 g, 0.002 mol), and 2-methyltetrahydrofuran (50 mL) was replaced by ethyl acetate (60 mL). The mixture was heated to reflux for ~16 hours.

Yield: 0.86 g (42.2% of theoretical value)

The same process as that in Example 5 was performed, except that tributylmethylammonium chloride (PTC, 0.53 g, 0.002 mol) was replaced by tetrabutylphosphine bromide (PTC, 1.53 g, 0.0045 mol), and 2-methyltetrahydrofuran (50 mL) was replaced by isobutyl acetate (50 mL). The mixture was heated to reflux for ~22 hours.

Yield: 1.34 g (65.7% of theoretical value)

EXAMPLE 6

Synthesis of 1-[(4-methyl-quinazolin-2-yl)methyl]-3-methyl-7-(2-butyn-1-yl)-8-(3-(R)-tert-butoxycarbonylaminopiperidin-1-yl)xanthine (Compound V)

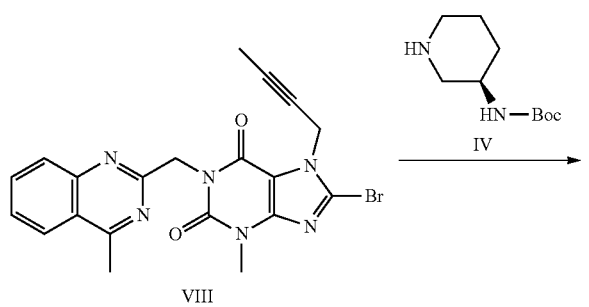

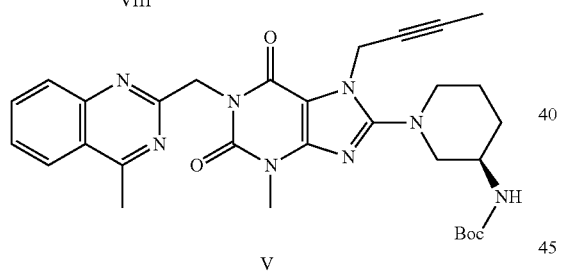

1-[(4-methyl-quinazolin-2-yl)methyl]-3-methyl-7-(2-butyn-1-yl)-8-bromoxanthine (Compound VIII, 1.86 g, 0.0041 mol), potassium carbonate (base 3, 0.85 g, 0.0062 mol), (R)-3-tert-butoxycarbonyl-aminopiperidine (Compound IV, 0.82 g, 0.0041 mol), tributylmethylammonium chloride (PTC, 0.09 g, 0.0004 mol) and 50 mL of toluene were added to a reaction flask. The mixture was heated to reflux for 8 to 10 hours, cooled to room temperature, added with 50 mL of water, stirred and filtered. The filter cake was dissolved in 50 mL of dichloromethane, and washed with 5% diluted HCl, water and saturated sodium chloride solution, respectively. The above dichloromethane solution was concentrated to give the xanthine precursor, i.e., 1-[(4-methyl-quinazolin-2-yl)methyl]-3-methyl-7-(2-butyn-1-yl)-8-(3-(R)-tert-butoxycarbonylaminopiperidin-1-yl)xanthine (Compound V).

Yield: 2.02 g (86.2% of theoretical value)

MS: $[M+H]^+$=573.4

$^1$H-NMR (400 MHz, DMSO): δ 1.39 (s, 9H), 1.63-1.70 (m, 1H), 1.76 (s, 3H), 1.76-1.85 (m, 2H), 2.84-2.88 (broad, s, CH3, CH, 4H), 3.00 (m, 1H), 3.34 (s, 1H), 3.39 (s, 3H), 3.56-3.59 (m, 2H), 3.65-3.68 (m, 1H), 4.87 (d, J=1.6 Hz, 2H), 5.32 (s, 2H), 7.02 (d, J=8.0 Hz, 1H), 7.66 (t, J=7.6 Hz, 1H), 7.80 (d, J=8.0 Hz, 1H), 7.90 (dd, J=7.2, 1.2 Hz, 1H), 8.23 (d, J=8.0 Hz, 1H).

The Compound V can also be prepared by the following processes.

The same process as that in Example 6 was performed, except that sodium iodide (cocatalyst $MX_5$, 0.06 g, 0.0004 mol) was additionally added. The mixture was heated to reflux for ~7 hours.

Yield: 1.96 g (83.7% of theoretical value)

The same process as that in Example 6 was performed, except that tributylmethylammonium chloride (PTC, 0.09 g, 0.0004 mol) was replaced by triethylamine (PTC, 0.08 g, 0.0008 mol). The mixture was heated to reflux for ~36 hours, cooled to room temperature, and added with 100 mL of water.

Yield: 1.06 g (45.3% of theoretical value)

The same process as that in Example 6 was performed, except that tributylmethylammonium chloride (PTC, 0.09 g, 0.0004 mol) was replaced by polyethylene glycol dimethyl ether (PTC, $CH_3O(CH_2CH_2O)_nCH_3$, n=3-8, 1.02 g, 0.0041 mol), and toluene (50 mL) was replaced by xylene (80 mL). The mixture was heated to reflux for ~18 hours, cooled to room temperature, and added with 100 mL of water.

Yield: 1.19 g (51.0% of theoretical value)

The same process as that in Example 6 was performed, except that tributylmethylammonium chloride (PTC, 0.09 g, 0.0004 mol) was replaced by tetrabutylphosphine bromide (PTC, 1.39 g, 0.0041 mol), and toluene (50 mL) was replaced by xylene (50 mL). The mixture was heated to reflux for ~48 hours.

Yield: 0.89 g (38.4% of theoretical value)

EXAMPLE 7

Synthesis of 3-methyl-7-(2-butyn-1-yl)-8-(3-(R)-tert-butoxycarbonylaminopiperidin-1-yl)-xanthine (Compound VIII-1)

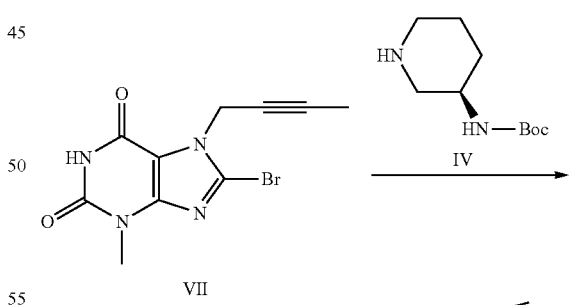

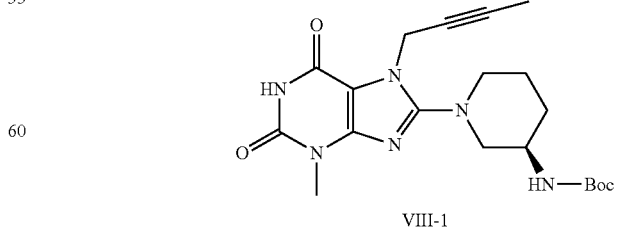

3-methyl-7-(2-butyn-1-yl)-8-bromoxanthine (Compound VII, 1.22 g, 0.0041 mol), potassium carbonate (base 2, 1.42 g, 0.0103 mol), (R)-3-tert-butoxycarbonylaminopiperidine (Compound IV, 0.821 g, 0.0041 mol), tetrabutylammonium bisulfate (PTC, 1.39 g, 0.0041 mol), potassium iodide (cocatalyst $MX_5$, 0.136 g, 0.00082 mol) and isopropyl acetate (50 mL) were added to a reaction flask. The mixture was heated to reflux for ~18 hours, cooled to room temperature, and added with 100 mL of water. After filtration, the filter cake was collected, and dried at 45° C. to give 3-methyl-7-(2-butyn-1-yl)-8-(3-(R)-tert-butoxycarbonylaminopiperidin-1-yl)xanthine (Compound VIII-1).

Yield: 1.54 g (90.5% of theoretical value)

MS: $[M+H]^+$=417.1

$^1$H-NMR (400 MHz, DMSO): δ1.39 (s, 9H), 1.63-1.70 (m, 1H), 1.77-1.83 (broad, m, CH3, CH2, 5H), 2.54 (s, 1H), 2.79-2.82 (m, 1H), 2.90-2.96 (m, 1H), 3.28 (s, 3H), 3.48-160 (m, 3H), 4.83 (s, 2H), 7.00 (d, J=7.2 Hz, 1H), 10.91 (s, 1H).

The Compound VIII-1 can also be prepared by the following processes.

The same process as that in Example 7 was performed, except that (R)-3-tert-butoxycarbonyl aminopiperidine (Compound IV, 0.821 g, 0.0041 mol) was replaced by (R)-3-tert-butoxycarbonylamino piperidine (Compound IV, 1.06 g, 0.0053 mol), and the potassium iodide (cocatalyst $MX_5$, 0.136 g, 0.00082 mol) was not added. The mixture was heated to reflux for ~36 hours.

Yield: 1.26 g (74.2% of theoretical value)

The same process as that in Example 7 was performed, except that potassium carbonate (base 2, 1.42 g, 0.0103 mol) was replaced by sodium carbonate (base 2, 1.30 g, 0.0123 mol), (R)-3-tert-butoxy carbonylaminopiperidine (Compound IV, 0.821 g, 0.0041 mol) was replaced by (R)-3-tert-butoxy carbonylaminopiperidine (Compound IV, 1.06 g, 0.0053 mol), tetrabutylammonium bisulfate (PTC, 1.39 g, 0.0041 mol) was replaced by triethylamine (PTC, 0.08 g, 0.0008 mol), isopropyl acetate (50 mL) was replaced by toluene (50 mL), and potassium iodide (cocatalyst $MX_5$, 0.136 g, 0.00082 mol) was not added. The mixture was heated to reflux for ~30 hours.

Yield: 0.46 g (27.5% of theoretical value)

The same process as that in Example 7 was performed, except that (R)-3-tert-butoxycarbonylaminopiperidine (Compound IV, 0.821 g, 0.0041 mol) was replaced by (R)-3-tert-butoxycarbonylaminopiperidine (Compound IV, 1.06 g, 0.0053 mol), tetrabutylammonium bisulfate (PTC, 1.39 g, 0.0041 mol) was replaced by polyethylene glycol dimethyl ether (PTC, $CH_3O(CH_2CH_2O)_nCH_3$, n=3-8, 1.02 g, 0.0041 mol), isopropyl acetate (50 mL) was replaced by xylene (80 mL), and potassium iodide (cocatalyst $MX_5$, 0.136 g, 0.00082 mol) was not added. The mixture was heated to reflux for ~40 hours, cooled to room temperature, and added with 150 mL of water.

Yield: 0.35 g (21.2% of theoretical value)

The same process as that in Example 7 was performed, except that potassium carbonate (base 2, 1.42 g, 0.0103 mol) was replaced by sodium carbonate (base 2, 1.30 g, 0.0123 mol), (R)-3-tert-butoxycarbonylaminopiperidine (Compound IV, 0.821 g, 0.0041 mol) was replaced by (R)-3-tert-butoxycarbonylaminopiperidine (Compound IV, 1.06 g, 0.0053 mol), tetrabutylammonium bisulfate (PTC, 1.39 g, 0.0041 mol) was replaced by tetrabutylphosphine bromide (PTC, 0.83 g, 0.0025 mol), isopropyl acetate (50 mL) was replaced by xylene (50 mL), and potassium iodide (cocatalyst $MX_5$, 0.136 g, 0.00082 mol) was not added. The mixture was heated to reflux for ~26 hours.

Yield: 0.57 g (33.7% of theoretical value)

EXAMPLE 8

Synthesis of 1-[(4-methyl-quinazolin-2-yl)methyl]-3-methyl-7-(2-butyn-1-yl)-8-(3-(R)-tert-butoxycarbonylaminopiperidin-1-yl)xanthine (Compound V)

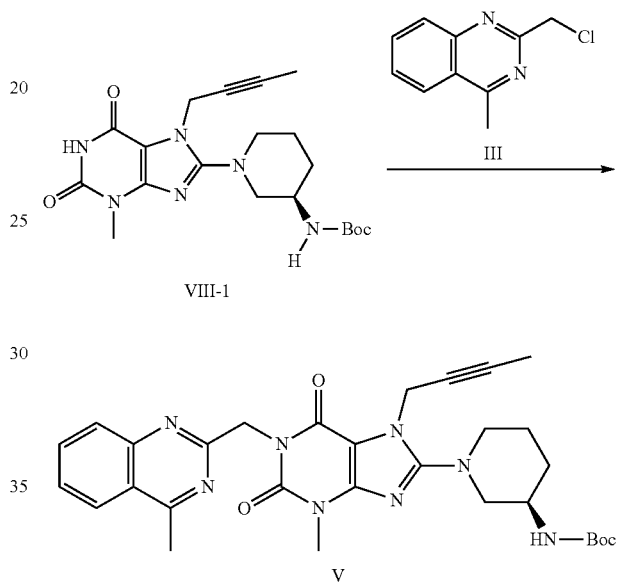

3-methyl-7-(2-butyn-1-yl)-8-(3-(R)-tert-butoxycarbonylaminopiperidin-1-yl)xanthine (Compound VIII-1, 1.3 g, 0.0031 mol), potassium carbonate (base 2, 1.28 g, 0.0093 mol), 2-chloromethyl-4-methylquinazoline (Compound III, 0.72 g, 0.0037 mol), tetrabutylammonium bromide (PTC, 0.49 g, 0.0015 mol) and cyclohexane (50 mL) were added to a reaction flask. The mixture was heated to reflux for ~15 hours, cooled to room temperature, and added with 100 mL of water. After filtration, the filter cake was collected, and dried at 45° C. to give 1-[(4-methyl-quinazolin-2-yl)methyl]-3-methyl-7-(2-butyn-1-yl)-8-(3-(R)-tert-butoxycarbonylamino piperidin-1-yl)xanthine (Compound V).

Yield: 1.43 g (80.3% of theoretical value)

MS: $[M+H]^+$=573.4

$^1$H-NMR (400 MHz, DMSO): δ 1.39 (s, 9H), 1.63-1.70 (m, 1H), 1.76 (s, 3H), 1.76-1.85 (m, 2H), 2.84-2.88 (broad, s, CH3, CH, 4H), 3.00 (m, 1H), 3.34 (s, 1H), 3.39 (s, 3H), 3.56-3.59 (m, 2H), 3.65-3.68 (m, 1H), 4.87 (d, J=1.6 Hz, 2H), 5.32 (s, 2H), 7.02 (d, J=8.0 Hz, 1H), 7.66 (t, J=7.6 Hz, 1H), 7.80 (d, J=8.0 Hz, 1H), 7.90 (dd, J=7.2, 1.2 Hz, 1H), 8.23 (d, J=8.0 Hz, 1H).

The Compound V can also be prepared by the following processes.

The same process as that in Example 8 was performed, except that 2-chloromethyl-4-methylquinazoline (Compound III, 0.72 g, 0.0037 mol) was replaced by 2-chloromethyl-4-methylquinazoline (Compound III, 0.66 g, 0.0034 mol), tetrabutylammonium bromide (PTC, 0.49 g, 0.0015 mol) was replaced by tetrabutylammonium bromide (PTC, 0.39 g, 0.0012 mol), and sodium iodide (cocatalyst $MX_5$, 0.09 g, 0.0006 mmol) was additionally added. The mixture was heated to reflux for ~18 hours.

Yield: 1.40 g (78.7% of theoretical value)

The same process as that in Example 8 was performed, except that 2-chloromethyl-4-methylquinazoline (Compound III, 0.72 g, 0.0037 mol) was replaced by 2-chloromethyl-4-methylquinazoline (Compound III, 0.83 g, 0.0043 mol), tetrabutylammonium bromide (PTC, 0.49 g, 0.0015 mol) was replaced by triethylamine (PTC, 0.06 g, 0.0006 mol), and cyclohexane (50 mL) was replaced by toluene (80 mL). The mixture was heated to reflux for ~40 hours, cooled to room temperature, and added with 150 mL of water.

Yield: 1.26 g (71.1% of theoretical value)

The same process as that in Example 8 was performed, except that tetrabutylammonium bromide (PTC, 0.49 g, 0.0015 mol) was replaced by polyethylene glycol dimethyl ether (PTC, $CH_3O(CH_2CH_2O)_nCH_3$, n=3-8, 0.54 g, 0.0021 mol), and cyclohexane (50 mL) was replaced by xylene (60 mL). The mixture was heated to reflux for ~19 hours, cooled to room temperature, and added with 130 mL of water.

Yield: 1.16 g (65.4% of theoretical value)

The same process as that in Example 8 was performed, except that 2-chloromethyl-4-methylquinazoline (Compound III, 0.72 g, 0.0037 mol) was replaced by 2-chloromethyl-4-methylquinazoline (Compound III, 0.83 g, 0.0043 mol), tetrabutylammonium bromide (PTC, 0.49 g, 0.0015 mol) was replaced by tetrabutylphosphine bromide (PTC, 1.05 g, 0.0031 mol), and cyclohexane (50 mL) was replaced by xylene (80 mL). The mixture was heated to reflux for ~40 hours, cooled to room temperature, and added with 150 mL of water.

Yield: 0.65 g (36.8% of theoretical value)

EXAMPLE 9

Synthesis of 1-[(4-methyl-quinazolin-2-yl)methyl]-3-methyl-7-(2-butyn-1-yl)-8-(3-(R)-phthalimidopiperidin-1-yl)xanthine (Compound V)

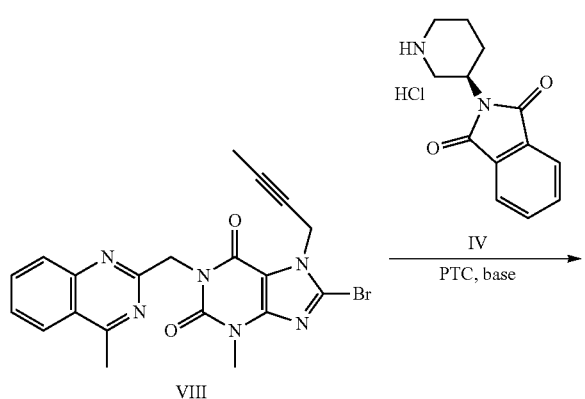

-continued

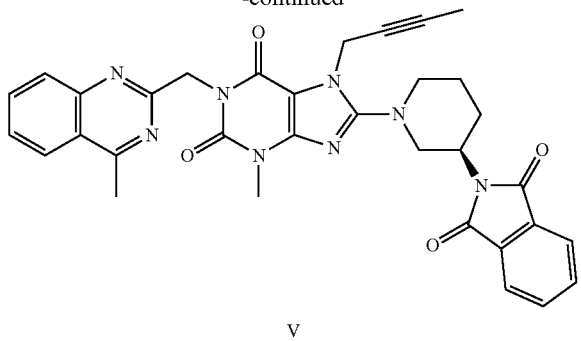

V

1-[(4-methyl-quinazolin-2-yl)methyl]-3-methyl-7-(2-butyn-1-yl)-8-bromoxanthine (Compound VIII, 1.86 g, 0.0041 mol), potassium carbonate (base, 2.27 g, 0.016 mol), (R)-3-phthalimidopiperidine hydrochloride (Compound IV, 1.2 g, 0.0045 mol) and isopropyl acetate (50 mL) were added to a reaction flask and stirred for 0.5 hours, followed by addition of trimethylbenzylammonium chloride (PTC, 0.23 g, 0.001 mol). The mixture in the reaction flask was heated to reflux for ~16 hours, cooled to room temperature, added with 50 mL of water, stirred and filtered. The filter cake was dissolved in 100 mL of dichloromethane, and washed with 5% diluted HCl, water and saturated sodium chloride solution, respectively. The above dichloromethane solution was concentrated to give the xanthine precursor, i.e. 1-[(4-methyl-quinazolin-2-yl)methyl]-3-methyl-7-(2-butyn-1-yl)-8-(3-(R)-phthalimido-piperidin-1-yl)xanthine.

Yield: 2.19 g (88.7% of theoretical value)
MS: $[M+H]^+=603.1$

The Compound V can also be prepared by the following process.

The same process as that in Example 9 was performed, except that sodium iodide (cocatalyst $MX_5$, 0.012 g, 0.082 mmol) was additionally added, and isopropyl acetate (50 mL) was replaced by ethyl acetate (50 mL) The mixture in the reaction flask was heated to reflux for ~12 hours, cooled to room temperature, and added with 50 mL of water.

Yield: 2.16 g (87.4% of theoretical value)
MS: $[M+H]^+=603.1$

EXAMPLE 10

Synthesis of 1-[(4-methyl-quinazolin-2-yl)methyl]-3-methyl-7-(2-butyn-1-yl)-8-(3-(R)-tert-butoxycarbonylaminopiperidin-1-yl)xanthine (Compound V) with "One-Pot Process"

Scheme 1:

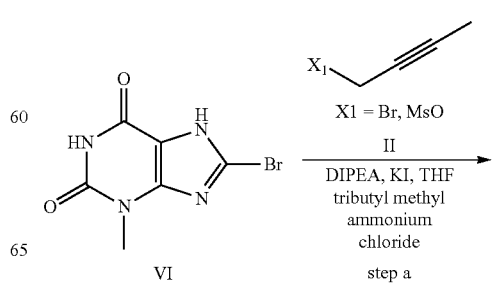

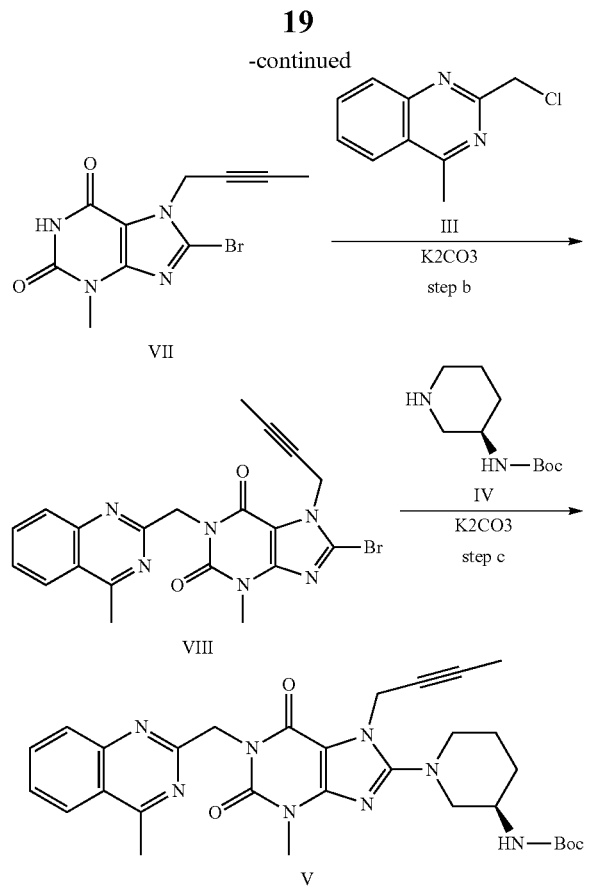

Step a: Synthesis of 3-methyl-7-(2-butyn-1-yl)-8-bromoxanthine (Compound VII)

8-bromo-3-methyl-1H-purine-2,6(3H,7H)-dione (Compound VI, prepared according to the process disclosed in *Journal of Medicinal Chemistry*, 2009, vol 52, No. 20, 6433-6445, 10 g, 0.041 mol), tetrahydrofuran (100 mL), di-isopropylethylamine (DIPEA, base 1, 6.84 g, 0.053 mol), 1-bromo-2-butyne (Compound II, 5.42 g, 0.041 mol) and potassium iodide (cocatalyst $MX_5$, 0.136 g, 0.82 mmol) were added to a reaction flask under nitrogen protection. Then tributylmethylammonium chloride (PTC, 4.7 g, 0.020 mol) was added to the above mixture. The mixture in the reaction flask was heated to reflux for ~18 hours. After cooled to room temperature, the mixture was directly used in the next step b.

Compound VII (3-methyl-7-(2-butyn-1-yl)-8-bromoxanthine) can also be prepared by another process as follows:

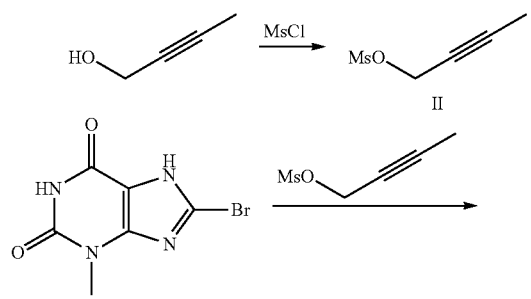

2-butyn-1-ol (2.27 g, 0.032 mol), tetrahydrofuran (THF, 80 ml) and triethylamine (3.92 g, 0.038 mol) were added to a reaction flask under nitrogen protection. The mixture was cooled to ~0° C., and added dropwise with methanesulfonyl chloride (4.08 g, 0.036 mol). After the addition, the reaction was conducted for ~1 hour.

8-bromo-3-methyl-1H-purine-2,6(3H,7H)-dione (Compound VI, prepared according to the process disclosed in *Journal of Medicinal Chemistry*, 2009, vol 52, No. 20, 6433-6445, 10 g, 0.041 mol), tetrahydrofuran (100 mL), di-isopropylethylamine (DIPEA, base 1, 6.84 g, 0.053 mol), 1-bromo-2-butyne (Compound II, 5.42 g, 0.041 mol) and potassium iodide (cocatalyst $MX_5$, 0.136 g, 0.82 mmol) were added to the reaction mixture. The mixture in the reaction flask was heated to reflux for ~18 hours. After cooled to room temperature, the mixture was directly used in the next step b.

Step b: Synthesis of 1-[(4-methyl-quinazolin-2-yl)methyl]-3-methyl-7-(2-butyn-1-yl)-8-bromo xanthine (Compound VIII)

Potassium carbonate (base 2, 14.15 g, 0.103 mol) and 2-chloromethyl-4-methylquinazoline (Compound III, 8.68 g, 0.045 mol) were added to the reaction mixture obtained in the step a. The mixture was heated to reflux for ~24 hours. After cooled to room temperature, the reaction mixture was directly used in the next step c.

Step c: Synthesis of 1-[(4-methyl-quinazolin-2-yl)methyl]-3-methyl-7-(2-butyn-1-yl)-8-(3-(R)-tert-butoxycarbonylaminopiperidin-1-yl)xanthine (Compound V)

Potassium carbonate (base 3, 8.49 g, 0.062 mol) and (R)-3-tert-butoxycarbonylaminopiperidine (Compound IV, 8.21 g, 0.041 mol) were added to the reaction mixture obtained in the step b. The mixture was heated to reflux for ~24 hours, cooled to room temperature, added with 50 mL of water, stirred and filtered. The filter cake was dissolved in 100 mL of dichloromethane, and washed with 5% diluted HCl, water and saturated sodium chloride solution, respectively. The above dichloromethane solution was concentrated to give the xanthine precursor, i.e. 1-[(4-methyl-quinazolin-2-yl)methyl]-3-methyl-7-(2-butyn-1-yl)-8-(3-(R)-tert-butoxycarbonylaminopiperidin-1-yl)xanthine (Compound V).

Yield: 16.08 g (68.9% of theoretical value)

MS: $[M+H]^+=573.4$

EXAMPLE 11

Synthesis of 1-[(4-methyl-quinazolin-2-yl)methyl]-3-methyl-7-(2-butyn-1-yl)-8-(3-(R)-tert-butoxycarbonylaminopiperidin-1-yl)xanthine (Compound V) with "One-Pot Process"

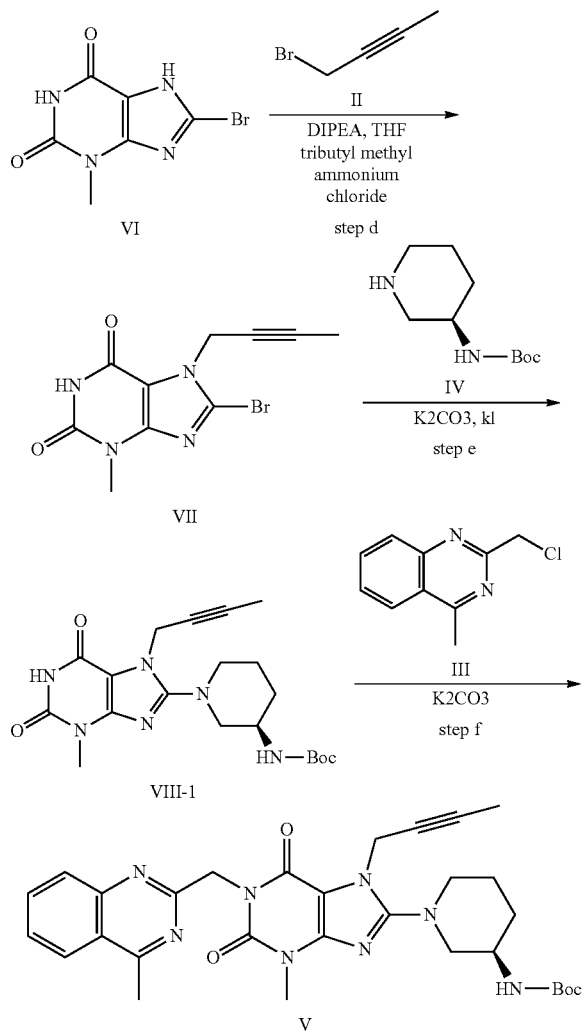

Scheme 2:

Step d: Synthesis of 3-methyl-7-(2-butyn-1-yl)-8-bromoxanthine (Compound VII)

8-bromo-3-methyl-1H-purine-2,6(3H,7H)-dione (Compound VI, prepared according to the process disclosed in *Journal of Medicinal Chemistry*, 2009, vol 52, No. 20, 6433-6445, 10 g, 0.041 mol), tetrahydrofuran (100 mL), di-isopropylethylamine (DIPEA, base 1, 6.84 g, 0.053 mol) and 1-bromo-2-butyne (Compound II, 5.42 g, 0.041 mol) were added to a reaction flask under nitrogen protection. Then tributylmethylammonium chloride (PTC, 4.7 g, 0.020 mol) was added to the above mixture. The mixture in the reaction flask was heated to reflux for ~18 hours. After cooled to room temperature, the reaction mixture was directly used in the next step e.

Step e: Synthesis of 3-methyl-7-(2-butyn-1-yl)-8-(3-(R)-tert-butoxycarbonylaminopiperidin-1-yl) xanthine (Compound VIII-1)

Potassium carbonate (base 2, 14.15 g, 0.103 mol), (R)-3-tert-butoxycarbonylaminopiperidine (Compound IV, 8.21 g, 0.041 mol) and potassium iodide (cocatalyst $MX_5$, 0.136 g, 0.82 mmol) were added to the reaction mixture obtained in the above step d. The mixture was heated to reflux for ~26 hours. After cooled to room temperature, the reaction mixture was directly used in the next step.

MS: $[M+H]^+$=417.1

Step f: Synthesis of 1-[(4-methyl-quinazolin-2-yl)methyl]-3-methyl-7-(2-butyn-1-yl)-8-(3-(R)-tert-butoxycarbonylaminopiperidin-1-yl)xanthine (Compound V)

Potassium carbonate (base 3, 8.49 g, 0.062 mol) and 2-chloromethyl-4-methylquinazoline (Compound III, 8.68 g, 0.045 mol) were added to the reaction mixture in the above step e. The mixture was heated to reflux for ~32 hours, cooled to room temperature, added with 50 mL of water, stirred and filtered. The filter cake was dissolved in 100 mL of dichloromethane, and washed with 5% diluted HCl, water and saturated sodium chloride solution, respectively. The above dichloromethane solution was concentrated to give the xanthine precursor, i.e. 1-[(4-methyl-quinazolin-2-yl)methyl]-3-methyl-7-(2-butyn-1-yl)-8-(3-(R)-tert-butoxycarbonylaminopiperidin-1-yl)xanthine.

Yield: 15.1 g (64.7% of theoretical value)
MS: $[M+H]^+$=573.4

EXAMPLE 12

Synthesis of 1-[(4-methyl-quinazolin-2-yl)methyl]-3-methyl-7-(2-butyn-1-yl)-8-(3-(R)-tert-butoxycarbonylaminopiperidin-1-yl)xanthine (Compound V) with "One-Pot Process"

The same process as that in Example 10 was performed, except that in the step a, tetrahydrofuran (100 mL) was replaced by ethyl acetate (100 mL), tributylmethylammonium chloride (PTC, 4.7 g, 0.020 mol) was replaced by tetrabutylammonium chloride (PTC, 0.56 g, 0.002 mol), and the mixture in the reaction flask was heated to reflux for ~38 hours;

in the step b, tetrabutylammonium hydroxide (PTC, 2.13 g, 0.0082 mol) was additionally added; and in the step c, the potassium hydroxide (base 3, 2.3 g, 0.041 mol) was additionally added.

Yield: 17.0 g (70% of theoretical value)
MS: $[M+H]^+$=573.4

EXAMPLE 13

Synthesis of 1-[(4-methyl-quinazolin-2-yl)methyl]-3-methyl-7-(2-butyn-1-yl)-8-(3-(R)-tert-butoxycarbonylaminopiperidin-1-yl)xanthine (Compound V) with "One-Pot Process"

The same process as that in Example 10 was performed, except that in the step a, 8-bromo-3-methyl-1H-purine-2,6(3H,7H)-dione (Compound VI, prepared according to the process disclosed in *Journal of Medicinal Chemistry*, 2009, vol 52, No. 20, 6433-6445, 10 g, 0.041 mol) was replaced by 8-bromo-3-methyl-1H-purine-2,6(3H,7H)-dione (Compound VI, prepared according to the process disclosed in *Journal of Medicinal Chemistry*, 2009, vol 52, No. 20, 6433-6445, 1.0 g, 0.004 mol), tetrahydrofuran (100 mL) was replaced by isoamylalcohol (30 mL), diisopropylethylamine (DIPEA, base 1, 6.84 g, 0.053 mol) was replaced by diisopropylethylamine (DIPEA, base 1, 0.68 g, 0.005 mol), 1-bromo-2-butyne (Compound II, 5.42 g, 0.041 mol) was replaced by 1-bromo-2-butyne (Compound II, 0.54 g, 0.004 mol), tributylmethylammonium chloride (PTC, 4.7 g, 0.020 mol) was replaced by tetrabutylammonium bisulfate (PTC, 0.68 g, 0.002 mol), and potassium iodide (cocatalyst $MX_5$, 0.136 g, 0.82 mmol) was replaced by potassium iodide (0.014 g, 0.082 mmol), and the mixture in the reaction flask was heated to reflux for ~5 hours;

in the step b, potassium carbonate (base 2, 14.15 g, 0.103 mol) was replaced by potassium carbonate (base 2, 1.42 g, 0.01 mol), and 2-chloromethyl-4-methylquinazoline (Compound III, 8.68 g, 0.045 mol) was replaced by 2-chloromethyl-4-methylquinazoline (Compound III, 0.87 g, 0.0045 mol), and the mixture was heated to reflux for ~10 hours; and in the step c, potassium carbonate (base 3, 8.49 g, 0.062 mol) was replaced by potassium carbonate (base 3, 0.85 g, 0.006 mol), and (R)-3-tert-butoxycarbonylaminopiperidine (Compound IV, 8.21 g, 0.041 mol) was replaced by (R)-3-tert-butoxycarbonylaminopiperidine (Compound IV, 0.82 g, 0.004 mol), and the mixture was heated to reflux for ~16 hours, cooled to room temperature, added with 30 mL of water, stirred and filtered, and the filter cake was dissolved in 50 mL of dichloromethane.

Yield: 1.56 g (67.2% of theoretical value)
MS: $[M+H]^+$=573.4

EXAMPLE 14

Synthesis of 1-[(4-methyl-quinazolin-2-yl)methyl]-3-methyl-7-(2-butyn-1-yl)-8-(3-(R)-tert-butoxycarbonylaminopiperidin-1-yl)xanthine (Compound V) with "One-Pot Process"

The same process as that in Example 10 was performed, except that in the step a, 8-bromo-3-methyl-1H-purine-2,6(3H,7H)-dione (Compound VI, prepared according to the process disclosed in *Journal of Medicinal Chemistry*, 2009, vol 52, No. 20, 6433-6445, 10 g, 0.041 mol) was replaced by 8-bromo-3-methyl-1H-purine-2,6(3H,7H)-dione (Compound VI, prepared according to the process disclosed in *Journal of Medicinal Chemistry*, 2009, vol 52, No. 20, 6433-6445, 1.0 g, 0.004 mol), tetrahydrofuran (100 mL) was replaced by xylene (50 mL), diisopropylethylamine (DIPEA, base 1, 6.84 g, 0.053 mol) was replaced by diisopropylethylamine (DIPEA, base 1, 0.68 g, 0.005 mol), 1-bromo-2-butyne (Compound II, 5.42 g, 0.041 mol) was replaced by 1-bromo-2-butyne (Compound II, 0.54 g, 0.004 mol), tributylmethylammonium chloride (PTC, 4.7 g, 0.020 mol) was replaced by polyethylene glycol dimethyl ether (PTC, $CH_3O(CH_2CH_2O)_nCH_3$, n=3-8, 1.0 g, 0.004 mol), and potassium iodide (cocatalyst $MX_5$, 0.136 g, 0.82 mmol) was replaced by potassium iodide (0.014 g, 0.082 mmol), and the mixture in the reaction flask was heated to reflux for ~36 hours;

in the step b, potassium carbonate (base 2, 14.15 g, 0.103 mol) was replaced by potassium carbonate (base 2, 1.42 g, 0.01 mol), and 2-chloromethyl-4-methylquinazoline (Compound III, 8.68 g, 0.045 mol) was replaced by 2-chloromethyl-4-methylquinazoline (Compound III, 0.87 g, 0.0045 mol), and the mixture was heated to reflux for ~28 hours; and in the step c, potassium carbonate (base 3, 8.49 g, 0.062 mol) was replaced by potassium carbonate (base 3, 0.85 g, 0.006 mol), and (R)-3-tert-butoxycarbonylaminopiperidine (Compound IV, 8.21 g, 0.041 mol) was replaced by (R)-3-tert-butoxycarbonylaminopiperidine (Compound IV, 0.82 g, 0.004 mol), the mixture was heated to reflux for ~48 hours, cooled to room temperature, added with 100 mL of water, stirred and filtered, and then the filter cake was dissolved in 50 mL of dichloromethane.

Yield: 0.49 g (21.2% of theoretical value)
MS: $[M+H]^+$=573.4

EXAMPLE 15

Synthesis of 1-[(4-methyl-quinazolin-2-yl)methyl]-3-methyl-7-(2-butyn-1-yl)-8-(3-(R)-tert-butoxycarbonylaminopiperidin-1-yl)xanthine (Compound V) with "One-Pot Process"

The same process as that in Example 10 was performed, except that in the step a, 8-bromo-3-methyl-1H-purine-2,6(3H,7H)-dione (Compound VI, prepared according to the process disclosed in *Journal of Medicinal Chemistry*, 2009, vol 52, No. 20, 6433-6445, 10 g, 0.041 mol) was replaced by 8-bromo-3-methyl-1H-purine-2,6(3H,7H)-dione (Compound VI, prepared according to the process disclosed in *Journal of Medicinal Chemistry*, 2009, vol 52, No. 20, 6433-6445, 1.0 g, 0.004 mol), tetrahydrofuran (100 mL) was replaced by isobutyl acetate (30 mL), diisopropylethylamine (DIPEA, base 1, 6.84 g, 0.053 mol) was replaced by diisopropylethylamine (DIPEA, base 1, 0.68 g, 0.005 mol), 1-bromo-2-butyne (Compound II, 5.42 g, 0.041 mol) was replaced by 1-bromo-2-butyne (Compound II, 0.54 g, 0.004 mol), tributylmethylammonium chloride (PTC, 4.7 g, 0.020 mol) was replaced by tetrabutylphosphine bromide (PTC, 0.68 g, 0.002 mol), and potassium iodide (cocatalyst $MX_5$, 0.136 g, 0.82 mmol) was replaced by potassium iodide (0.014 g, 0.082 mmol), and the mixture in the reaction flask was heated to reflux for ~5 hours;

in the step b, potassium carbonate (base 2, 14.15 g, 0.103 mol) was replaced by potassium carbonate (base 2, 1.42 g, 0.01 mol), and 2-chloromethyl-4-methylquinazoline (Compound III, 8.68 g, 0.045 mol) was replaced by 2-chloromethyl-4-methylquinazoline (Compound III, 0.87 g, 0.0045 mol), and the mixture was heated to reflux for ~6 hours; and in the step c, potassium carbonate (base 3, 8.49 g, 0.062 mol) was replaced by potassium carbonate (base 3, 0.85 g, 0.006 mol), and (R)-3-tert-butoxycarbonylaminopiperidine (Compound IV, 8.21 g, 0.041 mol) was replaced by (R)-3-tert-butoxycarbonylaminopiperidine (Compound IV, 0.82 g, 0.004 mol), the mixture was heated to reflux for ~16 hours, cooled to room temperature, added with 30 mL of water, stirred and filtered, and the filter cake was dissolved in 50 mL of dichloromethane.

Yield: 0.57 g (24.6% of theoretical value)
MS: $[M+H]^+$=573.4

EXAMPLE 16

Synthesis of 1-[(4-methyl-quinazolin-2-yl)methyl]-3-methyl-7-(2-butyn-1-yl)-8-(3-(R)-tert-butoxycarbonylaminopiperidin-1-yl)xanthine (Compound V) with "One-Pot Process"

The same process as that in Example 10 was performed, except that in the step a, 8-bromo-3-methyl-1H-purine-2,6(3H,7H)-dione (Compound VI, prepared according to the process disclosed in literature of *Journal of Medicinal Chemistry*, 2009, vol 52, No. 20, 6433-6445, 10 g, 0.041 mol) was replaced by 8-bromo-3-methyl-1H-purine-2,6(3H,7H)-dione (Compound VI, prepared according to the process disclosed in literature of *Journal of Medicinal Chemistry*, 2009, vol 52, No. 20, 6433-6445, 1.0 g, 0.004 mol), tetrahydrofuran (100 mL) was replaced by isopropyl acetate (30 mL), di-isopropylethylamine (DIPEA, base 1, 6.84 g, 0.053 mol) was replaced by di-isopropylethylamine (DIPEA, base 1, 0.68 g, 0.005 mol), 1-bromo-2-butyne (Compound II, 5.42 g, 0.041 mol) was replaced by 1-bromo-2-butyne (Compound II, 0.54 g, 0.004 mol), tributylmethylammonium chloride (PTC, 4.7 g, 0.020 mol) was replaced by tetrabutylammonium bromide (PTC, 1.29 g, 0.004 mol), and potassium iodide (cocatalyst $MX_5$, 0.136 g, 0.82 mmol) was replaced by potassium iodide (0.014 g, 0.082 mmol). The mixture in the reaction flask was heated to reflux for ~5 hours.

In the step b, potassium carbonate (base 2, 14.15 g, 0.103 mol) was replaced by potassium carbonate (base 2, 1.42 g, 0.01 mol), and 2-chloromethyl-4-methylquinazoline (Compound III, 8.68 g, 0.045 mol) was replaced by 2-chloromethyl-4-methylquinazoline (Compound III, 0.87 g, 0.0045 mol). The mixture was heated to reflux for ~6 hours.

In the step c, potassium carbonate (base 3, 8.49 g, 0.062 mol) was replaced by potassium carbonate (base 3, 0.85 g, 0.006 mol), and (R)-3-tert-butoxycarbonylaminopiperidine (Compound IV, 8.21 g, 0.041 mol) was replaced by (R)-3-tert-butoxycarbonylaminopiperidine (Compound IV, 0.82 g, 0.004 mol). The mixture was heated to reflux for ~14 hours, cooled to room temperature, and 30 mL of water was added.

Yield: 1.38 g (59.7% of theoretical value)
MS: $[M+H]^+=573.4$

EXAMPLE 17

Synthesis of 1-[(4-methyl-quinazolin-2-yl)methyl]-3-methyl-7-(2-butyn-1-yl)-8-(3-(S)-tert-butoxycarbonylaminopiperidin-1-yl)xanthine (Compound V) with "One-Pot Process"

Scheme 1:

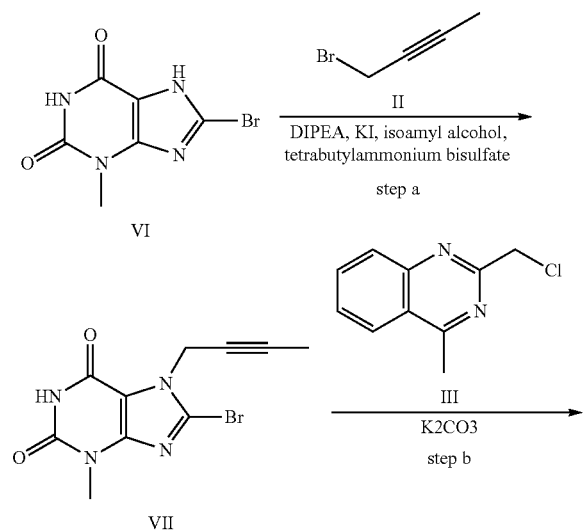

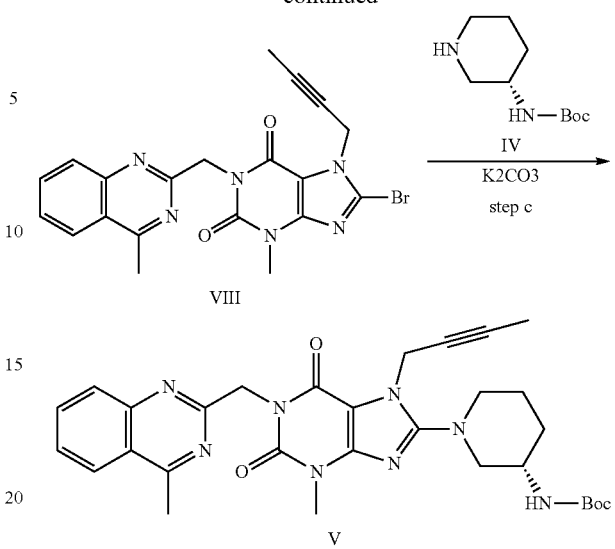

The same process as that in Example 10 was performed, except that in the step a, 8-bromo-3-methyl-1H-purine-2,6(3H,7H)-dione (Compound VI, prepared according to the process disclosed in *Journal of Medicinal Chemistry*, 2009, vol 52, No. 20, 6433-6445, 10 g, 0.041 mol) was replaced by 8-bromo-3-methyl-1H-purine-2,6(3H,7H)-dione (Compound VI, prepared according to the process disclosed in *Journal of Medicinal Chemistry*, 2009, vol 52, No. 20, 6433-6445, 1.0 g, 0.004 mol), tetrahydrofuran (100 mL) was replaced by isoamylalcohol (30 mL), di-isopropylethylamine (DIPEA, base 1, 6.84 g, 0.053 mol) was replaced by di-isopropylethylamine (DIPEA, base 1, 0.68 g, 0.005 mol), 1-bromo-2-butyne (Compound II, 5.42 g, 0.041 mol) was replaced by 1-bromo-2-butyne (Compound II, 0.54 g, 0.004 mol), tributylmethylammonium chloride (PTC, 4.7 g, 0.020 mol) was replaced by tetrabutylammonium bisulfate (PTC, 0.68 g, 0.002 mol), and potassium iodide (cocatalyst $MX_5$, 0.136 g, 0.82 mmol) was replaced by potassium iodide (0.014 g, 0.082 mmol), and the mixture in the reaction flask was heated to reflux for ~5 hours;

in the step b, potassium carbonate (base 2, 14.15 g, 0.103 mol) was replaced by potassium carbonate (base 2, 1.42 g, 0.01 mol), and 2-chloromethyl-4-methylquinazoline (Compound III, 8.68 g, 0.045 mol) was replaced by 2-chloromethyl-4-methylquinazoline (Compound III, 0.87 g, 0.0045 mol), and the mixture was heated to reflux for ~10 hours; and in the step c, potassium carbonate (base 3, 8.49 g, 0.062 mol) was replaced by potassium carbonate (base 3, 0.85 g, 0.006 mol), and (R)-3-tert-butoxycarbonylaminopiperidine (Compound IV, 8.21 g, 0.041 mol) was replaced by (S)-3-tert-butoxycarbonylaminopiperidine (Compound IV, 0.82 g, 0.004 mol), and the mixture was heated to reflux for ~16 hours, cooled to room temperature, added with 30 mL of water, stirred and filtered, and the filter cake was dissolved in 50 mL of dichloromethane.

Yield: 1.52 g (65% of theoretical value)
MS: $[M+H]^+=573.4$

EXAMPLE 18

Synthesis of 1-[(4-methyl-quinazolin-2-yl)methyl]-3-methyl-7-(2-butyn-1-yl)-8-(3-(R)-tert-butoxycarbonylaminopiperidin-1-yl)xanthine (Compound V) with "One-Pot Process"

The same process as that in Example 10 was performed, except that in the step a, tetrahydrofuran (100 mL) was replaced by methylisobutylketone (MIB K, 100 mL), tributylmethylammonium chloride (PTC, 4.7 g, 0.020 mol) was replaced by triethylamine (PTC, 0.83 g, 0.0082 mol), diisopropylethylamine (DIPEA, base 1, 6.84 g, 0.053 mol) was replaced by sodium bicarbonate (base 1, 6.9 g, 0.082 mol), 1-bromo-2-butyne (Compound II, 5.42 g, 0.041 mol) was replaced by 1-bromo-2-butyne (Compound II, 6.54 g, 0.049 mol), and the mixture in the reaction flask was heated to reflux for ~48 hours;

in the step b, potassium carbonate was not added, and benzyltrimethylammonium bromide (PTC, 0.94 g, 0.0041 mol) was additionally added, and the mixture was heated to reflux for ~36 hours; and in the step c, tetrabutylphosphine bromide (PTC, 1.39 g, 0.0041 mol) was additionally added, and the mixture was heated to reflux for ~48 hours, cooled to room temperature, added with 50 mL of water, stirred and filtered, and the filter cake was dissolved in 100 mL of dichloromethane.

Yield: 9.37 g (38.6% of theoretical value)

MS: [M+H]$^+$=573.4

EXAMPLE 19

Synthesis of 1-[(4-methyl-quinazolin-2-yl)methyl]-3-methyl-7-(2-butyn-1-yl)-8-(3-(R)-phthalimidopiperidin-1-yl)xanthine (Compound V) with "One-Pot Process"

Scheme 1

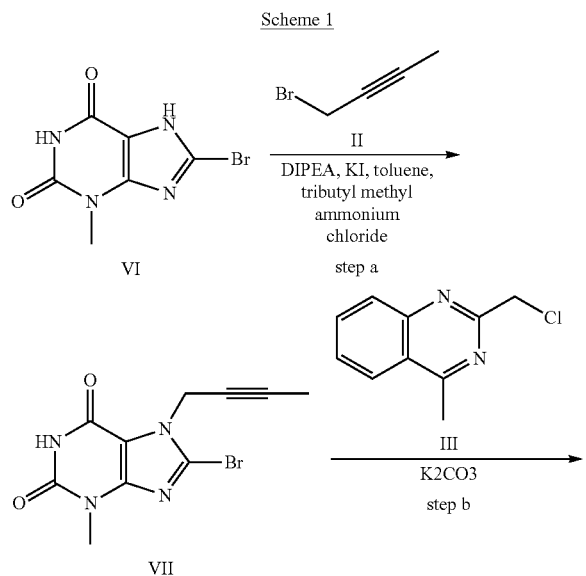

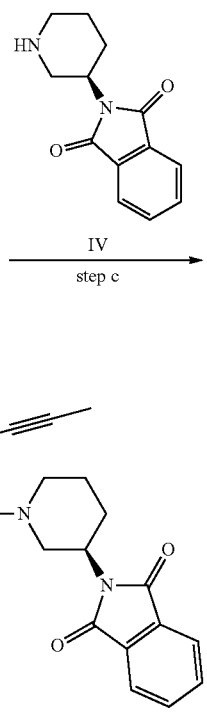

The same process as that in Example 10 was performed, except that in the step b, the mixture was heated to reflux for ~20 hours; and in the step c, potassium carbonate (base 3, 8.49 g, 0.062 mol) was replaced by potassium carbonate (base 3, 14.15 g, 0.103 mol), and (R)-3-tert-butoxycarbonylaminopiperidine (Compound IV, 8.21 g, 0.041 mol) was replaced by (R)-3-phthalimidopiperidine hydrochloride (Compound IV, 12.03 g, 0.045 mol), and the mixture in the reaction flask was heated to reflux for ~25 hours.

Yield: 17.42 g (74.6% of theoretical value)

MS: [M+H]$^+$=603.1

EXAMPLE 20

Synthesis of 1-[(4-methyl-quinazolin-2-yl)methyl]3-methyl-7-(2-butyn-1-yl)-8-(3-(R)-phthalimidopiperidin-1-yl)xanthine (Compound V) with "One-Pot Process"

Scheme 2:

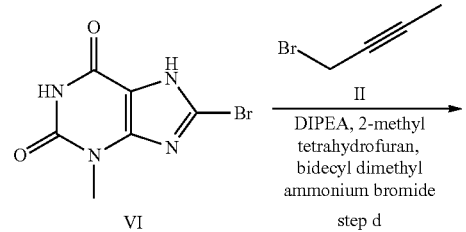

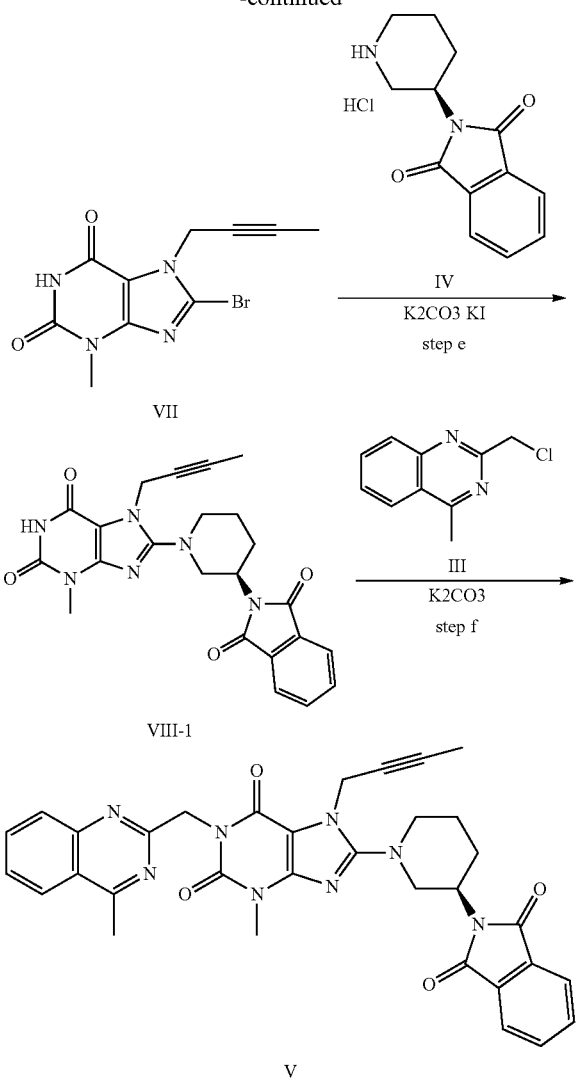

The same process as that in Example 11 was performed, except that in the step d, tetrahydrofuran (100 mL) was replaced by 2-methyltetrahydrofuran (100 mL), tributylmethylammonium chloride (PTC, 4.7 g, 0.020 mol) was replaced by didecyldimethylammonium bromide (PTC, 8.13 g, 0.020 mol), and potassium iodide (cocatalyst $MX_5$, 0.136 g, 0.82 mmol) was additionally added to the reaction flask under nitrogen protection, and the mixture in the reaction flask was heated to reflux for ~32 hours;

in the step e, potassium carbonate (base 2, 14.15 g, 0.103 mol) was replaced by potassium carbonate (base 2, 22.64 g, 0.165 mol), and (R)3-tert-butoxycarbonylaminopiperidine (Compound IV, 8.21 g, 0.041 mol) was replaced by (R)-3-phthalimidopiperidine hydrochloride (Compound IV, 12.03 g, 0.045 mol), and the mixture was heated to reflux for ~18 hours; and in the step f, the mixture is heated to reflux for ~25 hours.

Yield: 16.3 g (69.8% of theoretical value)

MS: $[M+H]^+=603.1$

EXAMPLE 21

Synthesis of 1-[(4-methyl-quinazolin-2-yl)methyl]-3-methyl-7-(2-butyn-1-yl)-8-(3-(R)-phthalimidopiperidin-1-yl)xanthine (Compound V) with "One-Pot Process"

The same process as that in Example 10 was performed, except that in step a, the tributylmethylammonium chloride (PTC, 4.7 g, 0.020 mol) was replaced by polyethylene glycol dimethyl ether (PTC, $CH_3O(CH_2CH_2O)_nCH_3$, n=3-8, 8.2 g, 0.032 mol), and the mixture in the reaction flask was heated to reflux for ~38 hours;

in the step b, potassium hydroxide (base 2, 1.15 g, 0.02 mol) was additionally added; and in the step c, potassium carbonate (base 3, 8.49 g, 0.062 mol) was replaced by potassium carbonate (base 3, 14.15 g, 0.103 mol) and potassium hydroxide (base 3, 1.15 g, 0.02 mol), and (R)-3-tert-butoxycarbonylaminopiperidine (Compound IV, 8.21 g, 0.041 mol) was replaced by (R)-3-phthalimidopiperidine hydrochloride (Compound IV, 12.03 g, 0.045 mol), and the reaction mixture was heated to reflux for ~40 hours.

Yield: 19.8 g (84.8% of theoretical value)

MS: $[M+H]^+=603.1$

EXAMPLE 22

Synthesis of 1-[(4-methyl-quinazolin-2-yl)methyl]-3-methyl-7-(2-butyn-1-yl)-8-(3-(R)-phthalimido-piperidin-1-yl)xanthine (Compound V) with "One-Pot Process"

The same process as that in Example 10 was performed, except that in step a, tributylmethylammonium chloride (PTC, 4.7 g, 0.020 mol) was replaced by tetrabutylphosphine bromide (PTC, 10.8 g, 0.032 mol), tetrahydrofuran (100 mL) was replaced by xylene (200 mL), and potassium iodide (cocatalyst $MX_5$, 0.136 g, 0.82 mmol) was not added;

in the step b, disodium hydrogen phosphate (base 2, 7.16 g, 0.02 mol) was additionally added, and the mixture was heated to reflux for ~20 hours, and in the step c, potassium carbonate (base 3, 8.49 g, 0.062 mol) was replaced by potassium carbonate (base 3, 22.67 g, 0.164 mol), and (R)-3-tert-butoxycarbonylaminopiperidine (Compound IV, 8.21 g, 0.041 mol) was replaced by (R)-3-phthalimido piperidine hydrochloride (Compound IV, 12.03 g, 0.045 mol), and the mixture was heated to reflux for ~40 hours, cooled to room temperature, and added with 100 mL of water.

Yield: 18.4 g (74.6% of theoretical value)

MS: $[M+H]^+=603.1$

EXAMPLE 23

Synthesis of 1-[(4-methyl-quinazolin-2-yl)methyl]-3-methyl-7-(2-butyn-1-yl)-8-(3-(R)-phthalimido-piperidin-1-yl)xanthine (Compound V) with "One-Pot Process"

The same process as that in Example 10 was performed, except that in the step a, tetrahydrofuran (100 mL) was replaced by ethyl acetate (150 mL), di-isopropylethylamine (DIPEA, base 1, 6.84 g, 0.053 mol) was replaced by triethylamine (base 1, 1.24 g, 0.012 mol) and sodium bicarbonate (base 1, 6.89 g, 0.082 mol), 1-bromo-2-butyne (Compound II, 5.42 g, 0.041 mol) was replaced by 1-bromo-2-butyne (Compound II, 6.54 g, 0.049 mol), tributylmethylammonium chloride (PTC, 4.7 g, 0.020 mol) was replaced by tetrabutylammonium hydroxide (PTC, 6.38 g, 0.025 mol), and potassium iodide as the cocatalyst was not added, and the mixture in the reaction flask was heated to reflux for ~28 hours, cooled to room temperature, and directly used in the next reaction step b;

in step b, the mixture was heated to reflux for ~28 hours; and in the step c, potassium carbonate (base 3, 8.49 g, 0.062 mol) was replaced by potassium carbonate (base 3, 22.67 g, 0.164 mol), and (R)-3-tert-butoxycarbonylaminopiperidine (Compound IV, 8.21 g, 0.041 mol) was replaced by (R)-3-phthalimidopiperidine hydrochloride (Compound IV, 12.03 g, 0.045 mol), and the mixture was heated to reflux for ~40 hours, cooled to room temperature, and added with 100 mL of water.

Yield: 10.7 g (43.5% of theoretical value)
MS: [M+H]$^+$=603.1

EXAMPLE 24

Preparation of 1-[(4-methyl-quinazolin-2-yl)methyl]-3-methyl-7-(2-butyn-1-yl)-8-(3-(R)-amino piperidine-1-yl)xanthine (Compound I)

Process I:
Under nitrogen protection, 1-[(4-methyl-quinazolin-2-yl)methyl]-3-methyl-7-(2-butyn-1-yl)-8-(3-(R)-tert-butoxycarbonylaminopiperidin-1-yl)xanthine (5.0 g, 0.0087 mol) was added to 50 mL of dichloromethane, and stirred for dissolution. Trifluoroacetic acid (20 mL) was slowly added, and stirred at room temperature for 1-2 hours. 5 mL of water was added to the reaction mixture, and the organic phase was separated. The aqueous phase was washed with dichloromethane. The organic phase was combined, and washed triply with saturated sodium chloride solution. The dichloromethane solution was concentrated to give a crude 1-[(4-methyl-quinazolin-2-yl)methyl]-3-methyl-7-(2-butyn-1-yl)-8-(3-(R)-aminopiperidin-1-yl)xanthine.

The above crude 1-[(4-methyl-quinazolin-2-yl)methyl]-3-methyl-7-(2-butyn-1-yl)-8-(3-(R)-amino piperidin-1-yl) xanthine was dissolved in 20 times volume of methanol, added with activated carbon (10 to 25% by weight), and heated to reflux for 1 hour. The activated carbon was removed by hot filtration, and the filtrate was concentrated to obtain a residue. A mixed solvent of methylene chloride: methyl t-butyl ether=1:10 (v/v) was added to the concentrated residue, and the obtained mixture was stirred for 1 hour and filtered to obtain a filter cake, which was dried at 45° C. in a drying oven to give 1-[(4-methyl-quinazolin-2-yl)methyl]-3-methyl-7-(2-butyn-1-yl)-8-(3-(R)aminopiperidin-1-yl)xanthine (Compound I) with an optical purity of 100%.

Yield: 3.61 g (88% of theoretical value)
MS: [M+H]$^+$=473.3
Process II:

A solution of 1-[(4-methyl-quinazolin-2-yl)methyl]-3-methyl-7-(2-butyn-1-yl)-8(3-(R)-phthalimidopiperidin-1-yl)xanthine (3.6 g, 0.006 mol) in 36 mL of toluene was heated to 80-85° C. under nitrogen protection, followed by addition of 3.6 g (0.06 mol) of ethanolamine at 75-80° C. The mixture was stirred at 80-85° C. for 2 hours, and the mixture became clear. The toluene layer was separated and collected. The ethanolamine layer was washed twice with toluene (each 20 mL). The combined toluene layer was washed twice with water (40 mL) at 75-80° C. Toluene solution was collected and concentrated under reduced pressure, and toluene was distilled off. Methyl tert-butyl ether (40 mL) was added to the concentrated residue at 40-50° C., and cooled to 0-5° C. After filtration, the filter cake was collected. The obtained solid was dissolved in 20 times volume of methanol, added with activated carbon (10 to 25% by weight), and heated to reflux for 1 hour. The activated carbon was removed by hot filtration. The filtrate was concentrated to obtain a residue. A mixed solvent of methylene chloride:methyl t-butyl ether=1:10 was added to the concentrated residue, and the obtained mixture was stirred for 1 hour, filtered to obtain a filter cake, which was dried at 45° C. in a drying oven to give 1-[(4-methyl-quinazolin-2-yl)methyl]-3-methyl-7-(2-butyn-1-yl)-8-(3-(R)-aminopiperidin-1-yl)xanthine (Compound I) with an optical purity of 100%.

Yield: 2.35 g (83% of theoretical value)
Specific optical rotation $[\alpha]^{25}_D$=−20.1°, C=1, DMF
MS: [M+H]$^+$=473.3
$^1$H-NMR (400 MHz, DMSO): δ 1.19-1.31 (m, 1H), 1.57-1.69 (m, 1H), 1.77 (t, J=2.0 Hz, 3H), 1.75-1.83 (m, 1H), 1.84-1.92 (m, 1H), 2.75-2.88 (m, 2H), 2.89 (s, 3H), 2.97-3.06 (m, 1H), 3.36 (broad, s, 2H), 3.41 (s, 3H), 3.58-3.88 (m, 2H), 4.90 (s, 2H), 5.32 (s, 2H), 7.68 (dd, J=8.4, 6.8 Hz, 1H), 7.81 (d, J=8.3 Hz, 1H), 7.92 (dd, J=8.2 Hz, 1H), 8.25 (d, J=8.1 Hz, 1H).
$^{13}$C-NMR (100 MHz, DMSO): δ 3.03, 21.53, 23.25, 29.40, 33.08, 35.47, 45.53, 47.23, 49.55, 57.46, 73.72, 81.12, 103.19, 122.47, 125.71, 127.12, 127.85, 134.05, 147.74, 149.03, 150.93, 153.23, 156.14, 160.97, 168.82.

What is claimed is:
1. A process of preparing Compound V, wherein, in the presence of a phase transfer catalyst and a cocatalyst at a temperature of 0 to 160° C. in a solvent, Compound VI as a starting material reacts first with Compound II via 7-N-substitution reaction, then with (1) Compound III via 1-N-substitution reaction followed by Compound IV via 8-C-substitution reaction, or (2) Compound IV via 8-C-substitution reaction followed by Compound III via 1-N-substitution reaction, to give Compound V

V

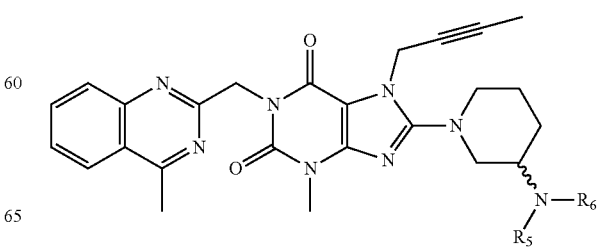

-continued

VI

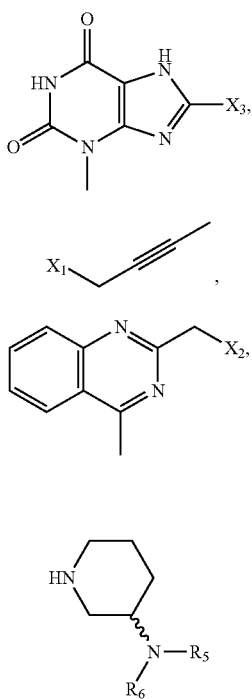

wherein, $X_1$, $X_2$ and $X_3$ are each a leaving group;

$R_5$ and $R_6$ are each a N-protecting group;

the phase transfer catalyst (PTC) is selected from the group consisting of:

(1) the phase transfer catalyst (PTC) has the structure of $R_1R_2R_3R_4N^+X_4^-$, wherein, $R_1$, $R_2$, $R_3$ and $R_4$ are each independently C1-C18 alkyl or C6-C18 aryl, $X_4$ is a halogen, bisulfate or hydroxy;

(2) the phase transfer catalyst (PTC) is a polyether;

(3) the phase transfer catalyst (PTC) is a tertiary amine of $R''_1R''_2R''_3N$, wherein, $R''_1$, $R''_2$ and $R''_3$ are each independently C1-C18 alkyl or C6-C18 aryl; or (4) the phase transfer catalyst (PTC) is a quaternary phosphine salt of $R'''_1R'''_2R'''_3R'''_4P^+X'^-_4$, wherein, $R'''_1$, $R'''_2$, $R'''_3$ and $R'''_4$ are each independently C1-C18 alkyl or C6-C18 aryl, $X'^-_4$ is halogen, or bisulfate;

wherein the phase transfer catalyst (PTC) is used in an amount of 0.05 to 1.0 molar equivalents based on the amount of the starting material of Compound VI;

wherein the cocatalyst has a structure of $\overset{M}{\oplus}\overset{X_5}{\ominus}$ wherein $X_5$ is an ion with negative charge, M is an ionic group with positive charge or a metal ion, and it is used in an amount of 0.01 to 1.0 molar equivalents based on the amount of the starting material of Compound VI, wherein the process further comprising a step of deprotecting the 3-amino of Compound V to give Compound I, the process is conducted according to the following Scheme 1 or Scheme 2:

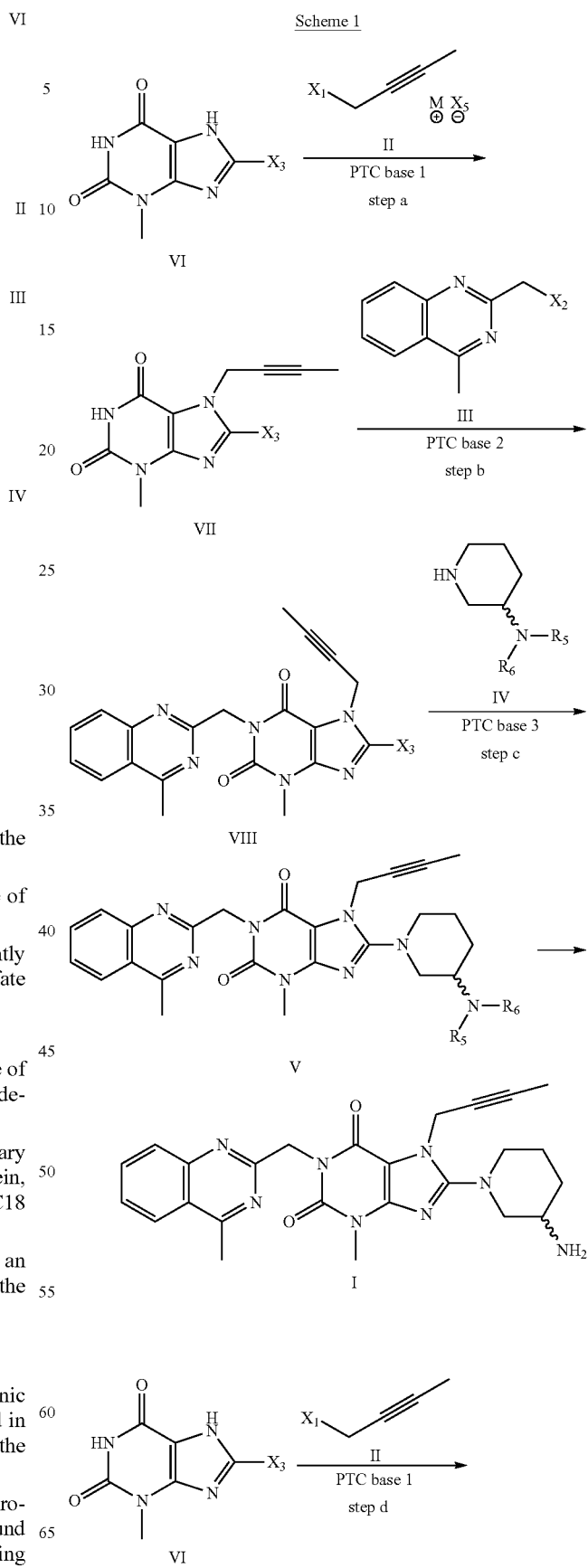

Scheme 1

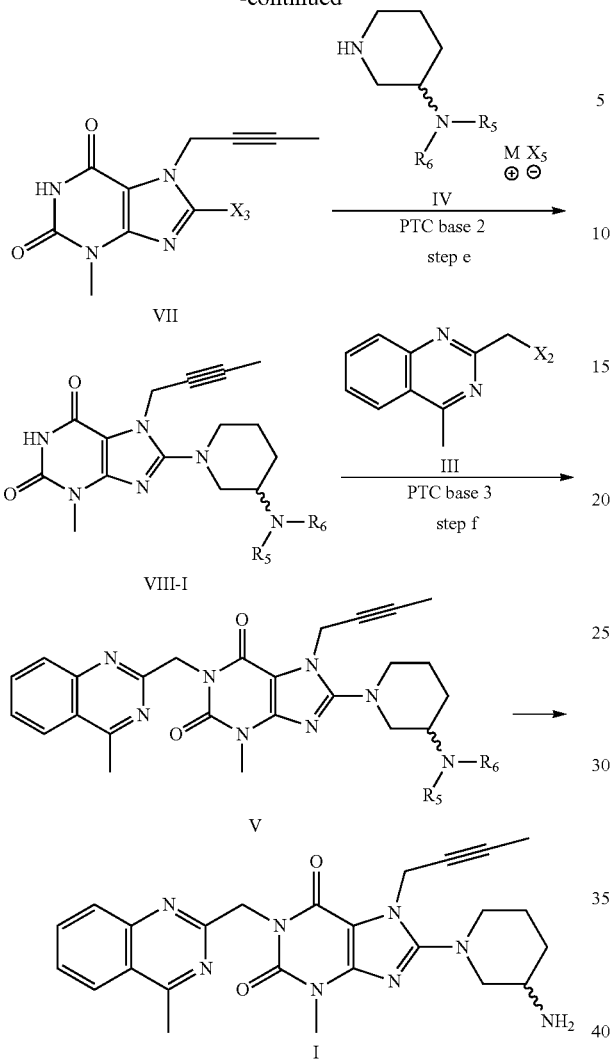

wherein, the base 1, base 2 and base 3 are an organic or inorganic base, and are each independently one or more selected from the group consisting of triethylamine (TEA), diisopropylethylamine (DIPEA), pyridine, NMP, DBU, N-methyl-morpholine, sodium carbonate, potassium carbonate, sodium bicarbonate, potassium bicarbonate, cesium carbonate, disodium hydrogen phosphate, sodium hydroxide, potassium hydroxide and sodium hydride, and wherein the PTC is selected to allow the reaction steps in the Scheme 1 or Scheme 2 to be conducted in a single solvent to realize a one-pot synthesis of Compound V.

2. The process according to claim 1, wherein, $X_1$, $X_2$ and $X_3$ are each independently selected from the group consisting of a halogen and a sulfonate group;

$R_5$ and $R_6$ are each independently H, C1-C16 alkoxycarbonyl, C6-C18 aryl C1-C16 alkoxycarbonyl, benzyl, p-methoxybenzyl, p-methylbenzyl, p-chlorobenzyl, p-bromobenzyl, p-nitrobenzyl, diphenylmethyl, 2,4-dimethoxybenzyl, 2-hydroxybenzyl, bis (4-methoxyphenyl) methyl, triphenylmethyl, (4-methoxyphenyl)diphenylmethyl, 9-phenylfluorenyl, formyl, acetyl, chloroacetyl, dichloroacetyl, trichloroacetyl, phenylacetyl, phenylpropionyl, benzoyl, p-phenylbenzoyl, phthaloyl, 4-nitrophthaloyl, dithiosuccinoyl, tetrachlorophthaloyl, p-toluenesulfonyl, benzenesulfonyl, methanesulfonyl, 2,4,6-trimethoxybenzenesulfonyl, pentamethylbenzenesulfonyl, 4-methoxybenzenesulfonyl, 2,4,6-trimethylbenzenesulfonyl, 2,6-dimethoxy-4-methyl-benzenesulfonyl, 2-nitrobenzenesulfonyl, 4-nitrobenzenesulfonyl, 2,4-dinitrobenzenesulfonyl, pyridine-2-sulfonyl, 2-(trisilyl)ethylsulfonyl, 9-anthracenesulfonyl, benzylsulfonyl, trifluoromethylsulfonyl, benzoylsulfonyl, or tert-butylsulfonyl;

the C1-C16 alkoxycarbonyl is methoxycarbonyl, ethoxycarbonyl, propoxycarbonyl, isopropoxycarbonyl, butoxycarbonyl, iso-butoxycarbonyl or tert-butoxycarbonyl;

the C6-C18 aryl C1-C16 alkoxycarbonyl is benzyloxycarbonyl or 9-fluorenylmethoxycarbonyl.

3. The process according to claim 1, wherein, the 3-amino in Compound IV is a chiral center, and Compound IV may be R-isomer, S-isomer or racemate.

4. The preparation process according to claim 1, wherein,

Compound IV is a free base or a piperidine salt foul ed with an organic or inorganic acid, the piperidine salt is one or more selected from the group consisting of hydrochloride, hydrobromide, phosphate, nitrate, sulfate, acetate, 2,2-dichloroacetate, adipate, ascorbate(D- or L-form thereof), aspartate, benzenesulfonate, benzoate, 4-acetamidobenzoate, camphoricate, camphor-10-sulfonate, decanoic acid salt (caprate), hexanoic acid salt (caproate), octanoic acid salt (caprylate), carbonate, cinnamate, citrate, cyclamate, dodecyl sulfate, ethane-1,2-disulfonate, ethanesulfonate, 2-hydroxyethanesulfonate, foilliate, fumarate, mucic acid salt, gentisic acid salt, glucoheptonic acid salt, gluconate, glucuronate, glutamate, glutarate, 2-oxo-glutarate, glycerophosphate, glycolate, hippurate, isobutyrate, lactate, lactobionic acid salt, laurate, maleate, malate, malonate, mandelate, methanesulfonate, naphthalene-1,5-disulfonate, naphthalene-2-sulfonate, 1-hydroxy-2-naphthoate, nicotinate, oleate, orotic acid salt, oxalate, palmitate, dihydroxy naphthoic acid salt, propionate, pyroglutamate, salicylate, 4-aminosalicylate, sebacate, stearate, succinate, tartrate, thiocyanate, tosylate and undecylenic acid salt.

5. The process according to claim 1, wherein, (1) when the phase transfer catalyst (PTC) has the structure of $R_1R_2R_3R_4N^+X_4^-$, it is one or more compounds selected from the group consisting of cetyltrimethylammonium bromide, dicetyldimethylammonium bromide, dicetyldimethylammonium chloride, dioctadecyldimethylammonium bromide, dioctadecyldimethylammonium chloride, benzyltriethylammonium chloride, tributylmethylammonium chloride, tributylmethylammonium bromide, triethylammoniumbromide, triethylammonium chloride, tripropylmethylammonium chloride, trioctylmethylammonium chloride, myristyltrimethylammonium chloride, tripropylmethylammonium bromide, tetrapropylammonium chloride, tetrapropylammonium bromide, tetraethylammonium bromide, tetraethylammonium chloride, tetrabutylammonium bisulfate, didecyldimethylammonium chloride, didecyldimethylammonium bromide, tetrabutylammonium bromide, benzyltributylammonium chloride and benzyltributylammonium bromide; or one or more selected from the group consisting of tetramethylammonium hydroxide, trimethylethylammonium hydroxide, tetrabutylammonium hydroxide and trimethylbenzylammonium hydroxide;

(2) when the phase transfer catalyst (PTC) is a polyether, it is linear polyethylene glycol of $H(OCH_2CH_2)_nOH$, or a linear polyethylene glycol dialkyl ether of $R'_1(OCH_2CH_2)_nOR'_2$; wherein, $R'_1$ and $R'_2$ are each independently C1-C18 alkyl or C6-C18 aryl, n is an integer of 1-44;

(3) when the phase transfer catalyst (PTC) is a tertiary amine of $R''_1R''_2R''_3N$, it is pyridine or triethylamine;

(4) when the phase transfer catalyst (PTC) is a quaternary phosphine salt of $R'''_1R'''_2R'''_3R'''_4P^+X'^-_4$, it is one or more selected from the group consisting of triphenylmethylphosphine bromide, triphenylmethylphosphine chloride, triphenylethylphosphine chloride, triphenylethylphosphine bromide, triphenylpropylphosphine chloride, triphenylpropylphosphine bromide, triphenylbenzylphosphine chloride, triphenylbenzylphosphine bromide, triphenyldodecylphosphine chloride, triphenyldodecylphosphine bromide, triphenylcetylphosphine chloride, triphenylcetylphosphine bromide, tetrabutylphosphine bromide, tetrabutylphosphine chloride, tetraphenylphosphine bromide and cetyltributylphosphine bromide;

the phase transfer catalyst (PTC) is used in an amount of 0.2 to 0.5 molar equivalents based on the amount of the starting material of Compound VI.

6. The process according to claim 1, wherein, in the cocatalyst of $\overset{M}{\oplus}\overset{X_5}{\ominus}$ $X_5$ is a halogen ion; and M is $NH_4^+$ or an alkali metal ion.

7. The process according to claim 1, wherein, steps a-f include the use of one or more solvents selected from the group consisting of tetrahydrofuran, 2-methyltetrahydrofuran, methyl isobutyl ketone, n-butanol, t-butanol, isoamyl alcohol, toluene, xylene, chlorobenzene, ethyl acetate, isopropyl acetate, propyl acetate, butyl acetate, isobutyl acetate, methyl tert-butyl ether, isopropyl ether, diphenyl ether, cyclohexane, n-hexane, n-heptane, mixed-heptane, iso-octane, acetonitrile, dichloromethane, chlorofoiiii, and 1,2-dichloroethane.

8. A process of preparing Compound V, wherein, in the presence of a phase transfer catalyst and a cocatalyst at a temperature of 0 to 160° C. in a solvent, Compound VI as a starting material reacts first with Compound II via 7-N-substitution reaction, then with (1) Compound III via 1-N-substitution reaction followed by Compound IV via 8-C-substitution reaction, or (2) Compound IV via 8-C-substitution reaction followed by Compound III via 1-N-substitution reaction, to give Compound V

V

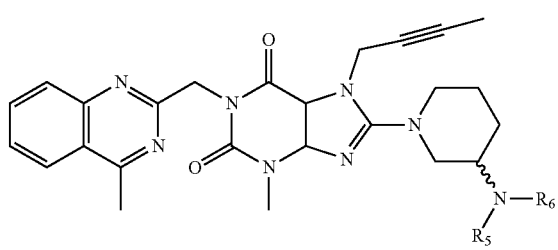

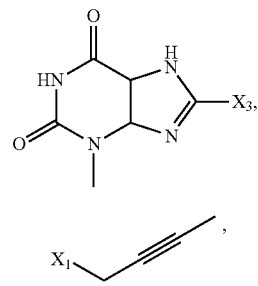

VI

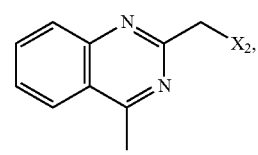

II

III

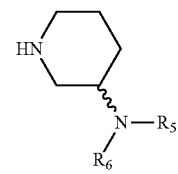

IV wherein, $X_1$, $X_2$ and $X_3$ are each a leaving group;

$R_5$ and $R_6$ are each a N-protecting group;

the phase transfer catalyst (PTC) is selected from the group consisting of:

(1) the phase transfer catalyst (PTC) has the structure of $R_1R_2R_3R_4N^+X_4^-$, wherein, $R_1$, $R_2$, $R_3$ and $R_4$ are each independently C1-C18 alkyl or C6-C18 aryl, $X_4$ is a halogen, bisulfate or hydroxy;

(2) the phase transfer catalyst (PTC) is a polyether;

(3) the phase transfer catalyst (PTC) is a tertiary amine of $R''_1R''_2R''_3N$, wherein, $R''_1$, $R''_2$ and $R''_3$ are each independently C1-C18 alkyl or C6-C18 aryl; or (4) the phase transfer catalyst (PTC) is a quaternary phosphine salt of $R'''_1R'''_2R'''_3R'''_4P^+X''^-_4$, wherein, $R'''_1$, $R'''_2$, $R'''_3$ and $R'''_4$ are each independently C1-C18 alkyl or C6-C18 aryl, $X'^-_4$ is halogen, or bisulfate;

wherein the phase transfer catalyst (PTC) is used in an amount of 0.05 to 1.0 molar equivalents based on the amount of the starting material of Compound VI;

wherein the cocatalyst has a structure of $\overset{M}{\oplus}\overset{X_5}{\ominus}$ wherein $X_5$ is an ion with negative charge, M is an ionic group with positive charge or a metal ion, and it is used in an amount of 0.01 to 1.0 molar equivalents based on the amount of the starting material of Compound VI, wherein the process further comprising a step of deprotecting the 3-amino of Compound V to give Compound I, the process is conducted according to the following Scheme 1 or Scheme 2:

Scheme 1

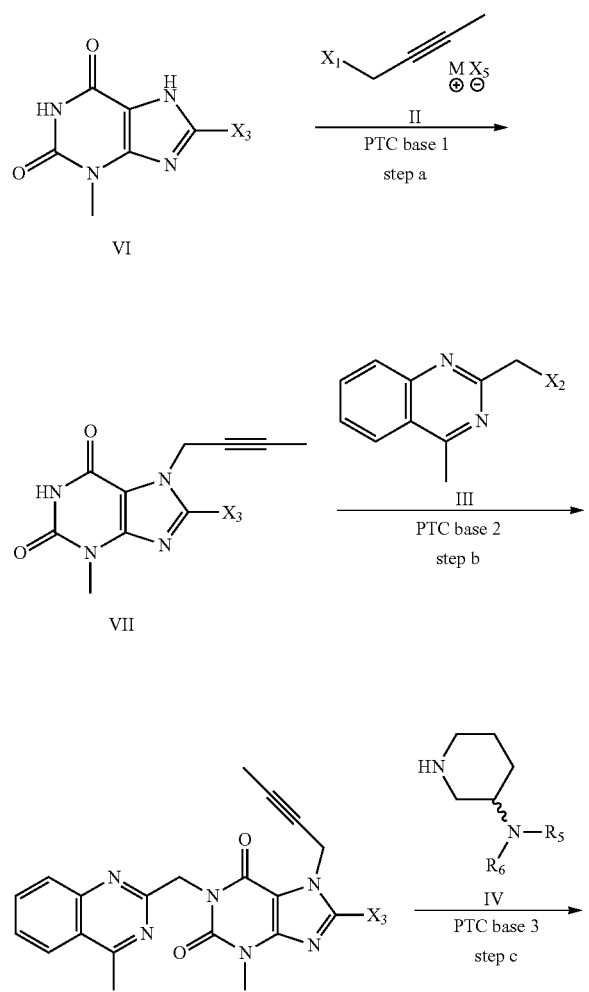

Scheme 2

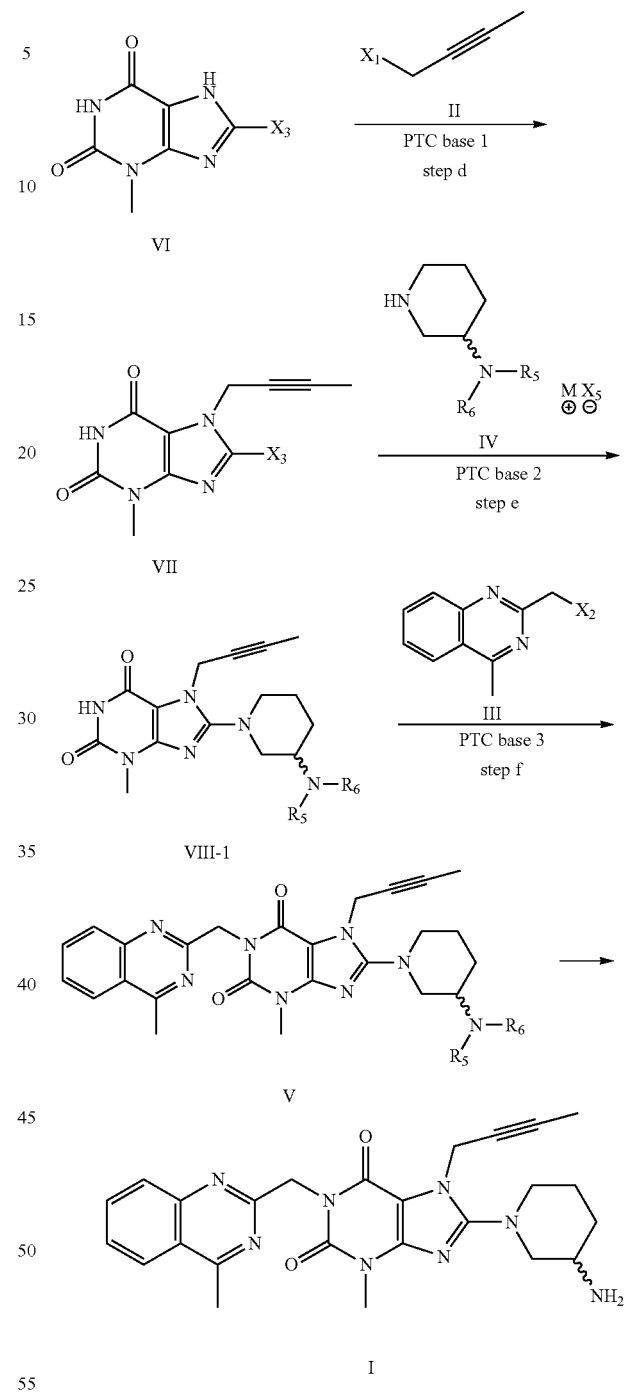

wherein, the base 1, base 2 and base 3 are an organic or inorganic base, and are each independently one or more selected from the group consisting of triethylamine (TEA), diisopropylethylamine (DIPEA), pyridine, NMP, DBU, N-methyl-morpholine, sodium carbonate, potassium carbonate, sodium bicarbonate, potassium bicarbonate, cesium carbonate, disodium hydrogen phosphate, sodium hydroxide, potassium hydroxide and sodium hydride, wherein the PTC is selected to allow the reaction steps in the Scheme 1 or Scheme 2 to be conducted in a single solvent to realize a one-pot synthesis of Compound V, and wherein, the molar ratio of the reactants in steps a and d is VI: II: base 1=1: (0.8 to 1.5): (1.0 to 5.0); and the reaction time is 0.5 to 48 hours;

the molar ratio of the reactants in step b is VII: III: base 2=1.0: (0.8 to 1.5): (1.0 to 5.0); and the reaction time is 0.5 to 48 hours;

the molar ratio of the reactants in step c is VIII: IV: base 3=1.0: (0.8 to 1.5): (1.0 to 5.0); and the reaction time is 0.5 to 72 hours;

the molar ratio of the reactants in step e is VII: IV: base 2=1.0: (0.8 to 1.5): (1.0 to 5.0); and the reaction time is 0.5 to 72 hours; and the molar ratio of the reactants in step f is VIII-1: III: base 3=1.0: (0.8 to 1.5): (1.0 to 5.0); and the reaction time is 0.5 to 72 hours.

9. The process according to claim 1, wherein, in the presence of a phase transfer catalyst and a cocatalyst at a temperature of 40 to 120° C. in a solvent, Compound VI as a starting material reacts with Compound II via 7-N-substitution reaction, with Compound III via 1-N-substitution reaction, and then with Compound IV via 8-C-substitution reaction, to give Compound V.

10. The process according to claim 1, wherein, the halogen in $X_4$ and $X'_4$ are each independently fluorine, chlorine or bromine.

11. The process according to claim 2, wherein, the halogen is fluorine, chlorine or bromine, the sulfonate group is methylsulfonyloxy, phenylsulfonyloxy, p-toluenesulfonyloxy, p-chlorophenylsulfonyloxy, benzylsulfonate, 2-(4-nitrophenylethyl)sulfonate or trifluoromethylsulfonyloxy.

12. The process according to claim 2, wherein, $X_1$ is bromine, $X_2$ is chlorine, $X_3$ is bromine or chlorine.

13. The process according to claim 6, wherein, the halogen ion is iodine or bromine ion.

14. The process according to claim 6, wherein, the alkali metal ion is potassium or sodium ion.

15. The process according to claim 6, wherein, the cocatalyst is lithium bromide, sodium bromide, potassium bromide, lithium iodide, sodium iodide, ammonium chloride, sodium bromide, ammonium iodide or potassium iodide.

* * * * *